US012243631B2

(12) United States Patent
Anderson

(10) Patent No.: US 12,243,631 B2
(45) Date of Patent: *Mar. 4, 2025

(54) DEVICES, SYSTEMS, AND METHODS FOR VESSEL ASSESSMENT AND INTERVENTION RECOMMENDATION

(71) Applicant: PHILIPS IMAGE GUIDED THERAPY CORPORATION, San Diego, CA (US)

(72) Inventor: David Anderson, Temecula, CA (US)

(73) Assignee: PHILIPS IMAGE GUIDED THERAPY CORPORATION, San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/722,891

(22) Filed: Apr. 18, 2022

(65) Prior Publication Data

US 2022/0246271 A1 Aug. 4, 2022

Related U.S. Application Data

(63) Continuation of application No. 14/961,505, filed on Dec. 7, 2015, now Pat. No. 11,309,071.

(Continued)

(51) Int. Cl.
*A61B 6/00* (2024.01)
*A61B 5/0215* (2006.01)
(Continued)

(52) U.S. Cl.
CPC ........... *G16H 20/40* (2018.01); *A61B 5/0215* (2013.01); *A61B 6/032* (2013.01); *A61B 6/4417* (2013.01);
(Continued)

(58) Field of Classification Search
CPC ....... A61B 6/032; A61B 6/4417; A61B 6/504; A61B 6/5217; A61B 8/04; A61B 8/12
See application file for complete search history.

(56) References Cited

U.S. PATENT DOCUMENTS 6,930,014 B2  8/2005  Kim
7,930,014 B2  4/2011  Huennekens
(Continued)

FOREIGN PATENT DOCUMENTS

WO  2006093776 A1  9/2006
WO  2013028612 A2  2/2013
WO  2014139024 A1  9/2014

OTHER PUBLICATIONS

Georgios Sianos et al "The Syntax Score: An Angiographic Tool Grading the Complexity of Coronary Artery Disease," EUROINTERVENTION, vol. 1, No. 2, 2005, pp. 219-227.
(Continued)

*Primary Examiner* — Rochelle D Turchen

(57) ABSTRACT

Devices, systems, and methods of evaluating risk associated with a condition of the vessel and providing an objective intervention recommendation based on the evaluated risk are disclosed. The method includes steps of obtaining physiologic measurements from a first instrument and a second instrument positioned within the vessel of the patient while the second instrument is moved longitudinally through the vessel from a first position to a second position, obtaining image data from an image of a vessel system, co-registering the physiologic measurements with the image data to produce co-registered physiologic measurements, and determining whether to perform a first surgical procedure or a second surgical procedure, wherein the determining is based on the co-registered physiologic measurements. Other associated methods, systems, and devices are also provided herein.

17 Claims, 11 Drawing Sheets

Related U.S. Application Data

(60) Provisional application No. 62/089,039, filed on Dec. 8, 2014.

(51) Int. Cl.
  *A61B 6/03* (2006.01)
  *A61B 6/50* (2024.01)
  *A61B 8/04* (2006.01)
  *A61B 8/12* (2006.01)
  *G16H 20/40* (2018.01)
  *G16H 50/30* (2018.01)
  *A61B 34/10* (2016.01)

(52) U.S. Cl.
  CPC ............ *A61B 6/504* (2013.01); *A61B 6/5217* (2013.01); *A61B 8/04* (2013.01); *A61B 8/12* (2013.01); *G16H 50/30* (2018.01); *A61B 2034/102* (2016.02); *A61B 2034/104* (2016.02); *A61B 2034/107* (2016.02); *A61B 2034/108* (2016.02)

(56) References Cited

U.S. PATENT DOCUMENTS

| | | |
|---|---|---|
| 8,548,778 B1 | 10/2013 | Hart |
| 8,824,752 B1 | 9/2014 | Fonte |
| 8,984,248 B2 | 3/2015 | Morishita |
| 10,052,031 B2 | 8/2018 | Sharma |
| 2003/0176778 A1* | 9/2003 | Messing ............... A61B 18/00 600/374 |
| 2008/0194806 A1 | 8/2008 | Yedgar |
| 2013/0046190 A1 | 2/2013 | Davies |
| 2013/0246034 A1 | 9/2013 | Sharma |
| 2014/0100451 A1 | 4/2014 | Tolkowsky |
| 2014/0114618 A1 | 4/2014 | Fonte |
| 2014/0194755 A1 | 7/2014 | Ide |
| 2014/0200867 A1 | 7/2014 | Lavi |
| 2015/0025330 A1 | 1/2015 | Davies |
| 2015/0066818 A1 | 3/2015 | Choi |
| 2015/0250438 A1* | 9/2015 | Bozkaya ............... A61B 6/5229 600/424 |
| 2015/0265162 A1 | 9/2015 | Lavi |
| 2015/0302139 A1 | 10/2015 | Sankaran |

OTHER PUBLICATIONS

Chang-Wook Nam, et al "Functional Syntax Score for Risk Assessment in Multivessel Coronary Artery Disease", Journal of American College of Cardiology, vol. 58, No. 12, 2011, pp. 1211-1218.

* cited by examiner

DEVICES, SYSTEMS, AND METHODS FOR VESSEL ASSESSMENT AND INTERVENTION RECOMMENDATION

CROSS REFERENCE TO RELATED APPLICATIONS

The present application is a continuation of U.S. patent application Ser. No. 14/961,505, filed Dec. 7, 2015, now U.S. Pat. No. 11,309,071, which claims priority to and the benefit of the U.S. Provisional Patent Application No. 62/089,039, filed Dec. 8, 2014, each of which is hereby incorporated by reference in its entirety.

TECHNICAL FIELD

The present disclosure relates generally to the assessment of vessels and, in particular, the assessment of the severity of a blockage or other restriction to the flow of fluid through a vessel and the treatment thereof. Aspects of the present disclosure are particularly suited for evaluation of biological vessels in some instances. For example, some particular embodiments of the present disclosure are specifically configured for the evaluation of human blood vessels.

BACKGROUND

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Common treatment options include percutaneous coronary intervention (PCI or angioplasty), stenting, or coronary artery bypass graft (CABG) surgery. As with all medical procedures, certain risks are associated with PCI, stenting, and CABG procedures. In order for a surgeon to make a better-informed decision regarding treatment options, additional information about the risk and likelihood of success associated with the treatment options is needed.

The severity of a stenosis is sometimes observed visually and roughly estimated based on experience. A patient's vasculature can be visualized using angiography. However, the locations of stenoses in a vessel can be difficult to visualize in a black and white angiographic image. The use of pressure data can improve the interpretation of information gleaned from an angiogram. Moreover, the severity of stenosis can also be better understood when efficiently visualized in relation to an angiographic image in connection with such data. Further, a more complete diagnosis of the patient can be made when the effects of both focal and diffuse stenoses are evaluated.

Accordingly, there remains a need for improved devices, systems, and methods for assessing the severity of a blockage in a vessel and, in particular, a stenosis in a blood vessel and for providing treatment best suited to the blockage in the vessel or blockages in the vessel system. Further, there remains a need for improved devices, systems, and methods of objectively evaluating risk associated with one or more treatment options and the likelihood of success those treatment options for the particular vessel.

SUMMARY

Embodiments of the present disclosure are directed to providing an objective recommendation of a treatment for a patient. One general aspect includes a method of recommending an intervention for a patient, including: co-registering a set of pressure measurements taken within a vessel system of the patient with image data of the vessel system to produce co-registered pressure measurements; calculating an image-based disease quantification score from the image data of the vessel system; modifying the image-based disease quantification score based on co-registered physiologic measurements to produce a functional disease quantification score; determining whether to perform a percutaneous coronary intervention or a coronary artery bypass graft (CABG), where the determining is based on the functional disease quantification score; and displaying an indication of the recommended intervention on a display.

Implementations may include one or more of the following features. The method where the indication of the recommended intervention identifies a CABG procedure when the functional disease quantification score is above a threshold. The method where the image-based disease quantification score includes a SYNTAX score and the function disease quantification score includes a functional SYNTAX score. The method where determining whether to perform the first surgical procedure or the second surgical procedure includes: interpreting, by a processing unit, the image data of the vessel system; identifying one or more lesions within the vessel system; and extracting, from the image data of the vessel system, physiology information.

Another general aspect includes a method of evaluating a vessel system of a patient to recommend an intervention for the patient, the method including: obtaining physiologic measurements from a first instrument and a second instrument positioned within the vessel of the patient while the second instrument is moved longitudinally through the vessel from a first position to a second position; obtaining image data from an image of a vessel system; co-registering the physiologic measurements with the image data to produce co-registered physiologic measurements; and calculating a disease quantification score, the disease quantification score indicating whether to perform a first surgical procedure or a second surgical procedure, where the calculating is based on the co-registered physiologic measurements.

Implementations may include one or more of the following features. The method where the image is an extravascular image. The method where co-registering the physiologic measurements with the image data to provide co-registered physiological measurements includes: associating, in a data file, each physiology measurement with a location within the vessel system. The method may also include identifying a corresponding location for each physiology measurement within the image data. The method may also include associating, in a co-registered physiologic measurements data file, each physiology measurement with its corresponding location within the image of the vessel system.

Implementations of the described techniques may include hardware, a method or process, or computer software on a computer-accessible medium. Other embodiments of this aspect include corresponding computer systems, apparatus, and computer programs recorded on one or more computer storage devices, each configured to perform the actions of the methods.

BRIEF DESCRIPTION OF THE DRAWINGS

Illustrative embodiments of the present disclosure will be described with reference to the accompanying drawings, of which.

Figure 1:
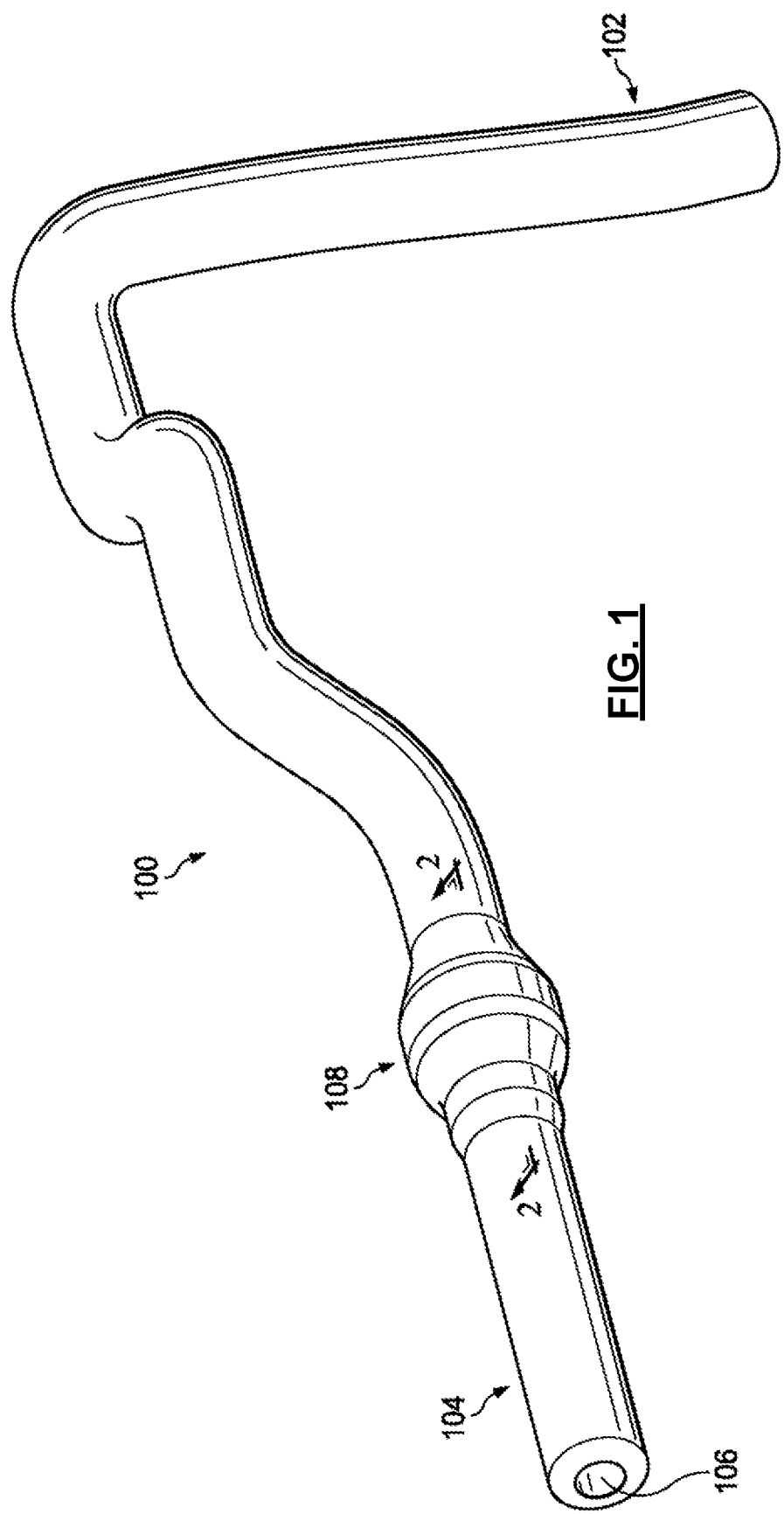
FIG. 1 is a diagrammatic perspective view of a vessel having a stenosis according to an embodiment of the present disclosure.

These drawings may be better understood by reference to the following detailed description.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Physiologic measurement data and the coronary angiogram typically behave as complementary, yet segregated sources of information. The coronary angiogram has been used to make treatment decisions. More recently, physiological data (including, but not limited to, pressure and/or flow measurements, both at hyperemia and rest) have shown that better decisions can be made based on the severity of a blockage by measuring the change in underlying physiological conditions from the beginning of a target artery to the end. Treating a patient based on the severity of this change or delta has shown to improve outcomes and reduce waste from unnecessary procedures. In one or more aspects of the present disclosure, the physiological data, as collected real-time, is linked or co-registered to a schematic of the coronary arteries or an angiogram. The data may also be visually depicted in a way that allows a clinician to interact and assess where severity changes, by sliding markings as placed on the image of the vessel and correlated with the collected physiological data. One or more embodiments described herein are also able to automatically make updates to the visual depiction based on the collected data as processed according to a risk calculator to provide a recommendation such as a particular intervention for a patient. For example, the data may be processed to provide an objective recommendation of whether to perform a percutaneous coronary intervention (PCI) or a coronary artery bypass graft (CABG) surgery.

One aspect of the present disclosure includes using a model of the patient's vasculature, obtained from angiography, to automatically calculate a disease quantification score. In this disclosure, the SYNTAX score is used as one example of such a disease quantification score. Other disease quantification scores may be used within the scope of this disclosure. One aspect of the present disclosure includes super-imposing real-time collected pressure and/or flow data (or other physiologic data) onto an angiogram, or a schematic of anatomy and representing the data in a way that helps a clinician determine how/where to intervene (including but not limited to using data to determine where to perform grafts (CABG planning) and PCI planning). One aspect of the present disclosure includes utilizing the collected pressure and/or flow data to automatically update the disease quantification score, thereby providing a functional disease quantification score. In some embodiments, the collected physiology data may include real-time data obtained during a procedure. One aspect of the present disclosure includes using the pressure, flow or other physiologic data with a computational algorithm to predict probabilities of graft patency and perfusion improvement during coronary artery bypass grafting (CABG). One aspect of the present disclosure includes processing the super-imposed physiologic data to isolate "regions of interest" where severity of physiologic data changes substantially for the purposes of determining how/where to intervene. One aspect of the present disclosure includes using the system-determined regions of interest to calculate a functional disease quantification score. Whether to perform a surgical procedure can be evaluated based on one or more of physiologic measurements, an image of the vessel with one or more visualizations, and relevant risk and perfusion calculations. A recommendation between one or more intervention options may be determined by the functional disease quantification score and presented to the clinician in a user interface.

In some embodiments, PCI planning is facilitated by the graphical overlay of physiologic data and the ability to add/delete and drag markings that allow the user to size and isolate blockages. Using a feature of a guide catheter and/or the guide wire as a calibrated and known length permits using these markings and co-registered physiologic data to estimate lesion lengths. These data can be inputted into a risk calculator including but not limited to a functional SYNTAX score. The use of the markings, length, and physiology data permit the interventionalist to plan a percutaneous coronary intervention whereby the number of stents and length of stents can be estimated. In some embodiments, the system may provide such a plan according to the functional disease quantification score and associated data.

In some embodiments, CABG planning is facilitated by the graphical overlay of physiologic data and the ability to add/delete and drag the markings that allow the user to size and isolate the blockages. In planning a bypass surgery (CABG), the data allows the physician to identify where on the artery the disease starts and stops. In some embodiments, the system may provide recommendations regarding the placement of such grafts. This results in a CABG plan, where the ideal placement of a graph can be determined and the prediction of graft patency and perfusion benefit can be identified to support decision making. The benefit of this is optimizing outcomes like graft patency and reducing costs like unnecessary grafting and time.

Figure 2:
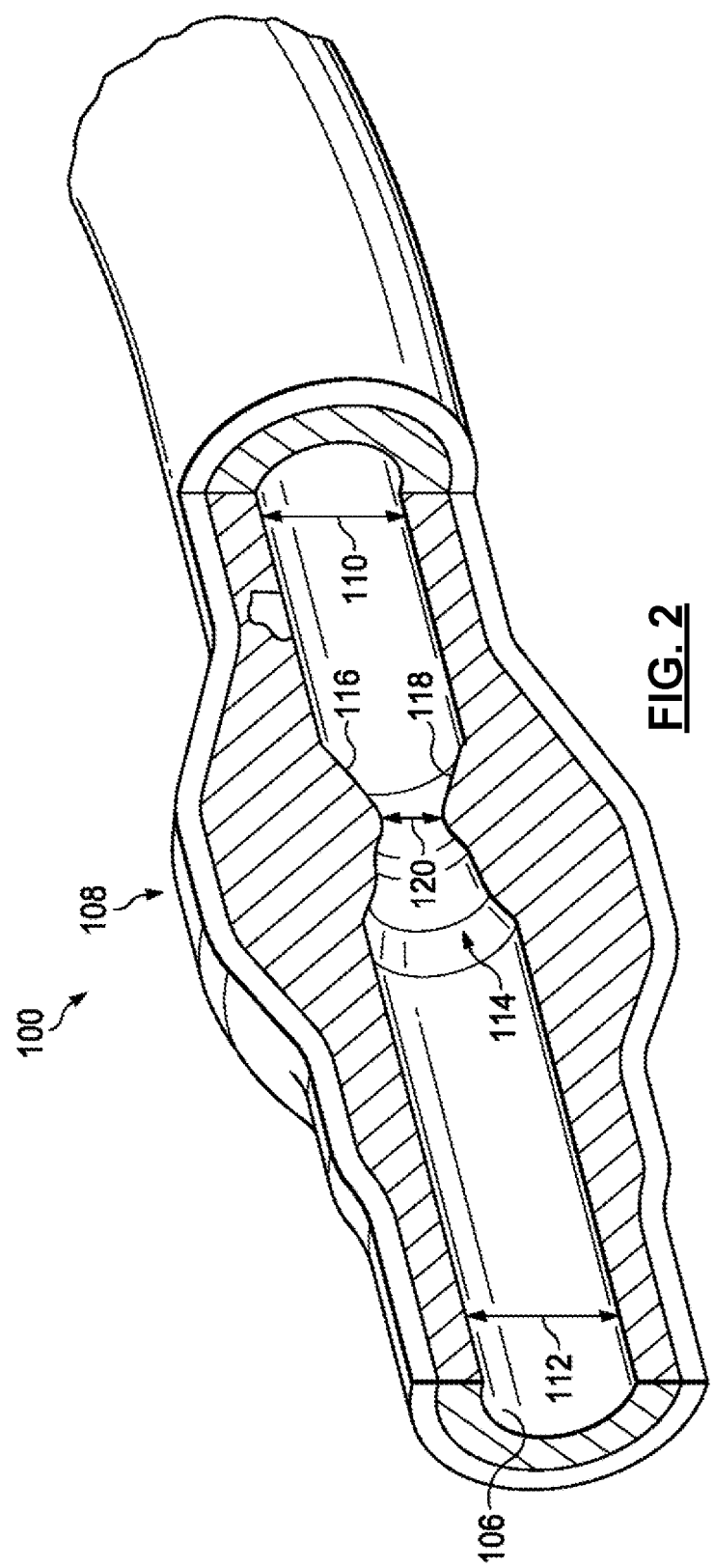
FIG. 2 is a diagrammatic, partial cross-sectional perspective view of a portion of the vessel of FIG. 1 taken along section line 2-2 of FIG. 1.

Referring to FIGS. 1 and 2, shown therein is a vessel 100 having a stenosis according to an embodiment of the present disclosure. In that regard, FIG. 1 is a diagrammatic perspective view of the vessel 100, while FIG. 2 is a partial cross-sectional perspective view of a portion of the vessel 100 taken along section line 2-2 of FIG. 1. Referring more specifically to FIG. 1, the vessel 100 includes a proximal portion 102 and a distal portion 104. A lumen 106 extends along the length of the vessel 100 between the proximal portion 102 and the distal portion 104. In that regard, the lumen 106 is configured to allow the flow of fluid through the vessel. In some instances, the vessel 100 is a blood vessel. In some particular instances, the vessel 100 is a coronary artery. In such instances, the lumen 106 is configured to facilitate the flow of blood through the vessel 100.

As shown, the vessel 100 includes a stenosis 108 between the proximal portion 102 and the distal portion 104. The stenosis 108 is generally representative of any blockage or other structural arrangement that results in a restriction to the flow of fluid through the lumen 106 of the vessel 100. Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 108 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 2, the lumen 106 of the vessel 100 has a diameter 110 proximal of the stenosis 108 and a diameter 112 distal of the stenosis. In some instances, the diameters 110 and 112 are substantially equal to one another. In that regard, the diameters 110 and 112 are intended to represent healthy portions, or at least healthier portions, of the lumen 106 in comparison to stenosis 108. Accordingly, these healthier portions of the lumen 106 are illustrated as having a substantially constant cylindrical profile and, as a result, the height or width of the lumen has been referred to as a diameter. However, it is understood that in many instances these portions of the lumen 106 will also have plaque buildup, a non-symmetric profile, and/or other irregularities, but to a lesser extent than stenosis 108 and, therefore, will not have a cylindrical profile. In such instances, the diameters 110 and 112 are understood to be representative of a relative size or cross-sectional area of the lumen and do not imply a circular cross-sectional profile.

As shown in FIG. 2, stenosis 108 includes plaque buildup 114 that narrows the lumen 106 of the vessel 100. In some instances, the plaque buildup 114 does not have a uniform or symmetrical profile, making angiographic evaluation of such a stenosis unreliable. In the illustrated embodiment, the plaque buildup 114 includes an upper portion 116 and an opposing lower portion 118. In that regard, the lower portion 118 has an increased thickness relative to the upper portion 116 that results in a non-symmetrical and non-uniform profile relative to the portions of the lumen proximal and distal of the stenosis 108. As shown, the plaque buildup 114 decreases the available space for fluid to flow through the lumen 106. In particular, the cross-sectional area of the lumen 106 is decreased by the plaque buildup 114. At the narrowest point between the upper and lower portions 116, 118 the lumen 106 has a height 120, which is representative of a reduced size or cross-sectional area relative to the diameters 110 and 112 proximal and distal of the stenosis 108. Note that the stenosis 108, including plaque buildup 114 is exemplary in nature and should be considered limiting in any way. In that regard, it is understood that the stenosis 108 has other shapes and/or compositions that limit the flow of fluid through the lumen 106 in other instances. While the vessel 100 is illustrated in FIGS. 1 and 2 as having a single stenosis 108 and the description of the embodiments below is primarily made in the context of a single stenosis, it is nevertheless understood that the devices, systems, and methods described herein have similar application for a vessel having multiple stenosis regions.

Figure 3:
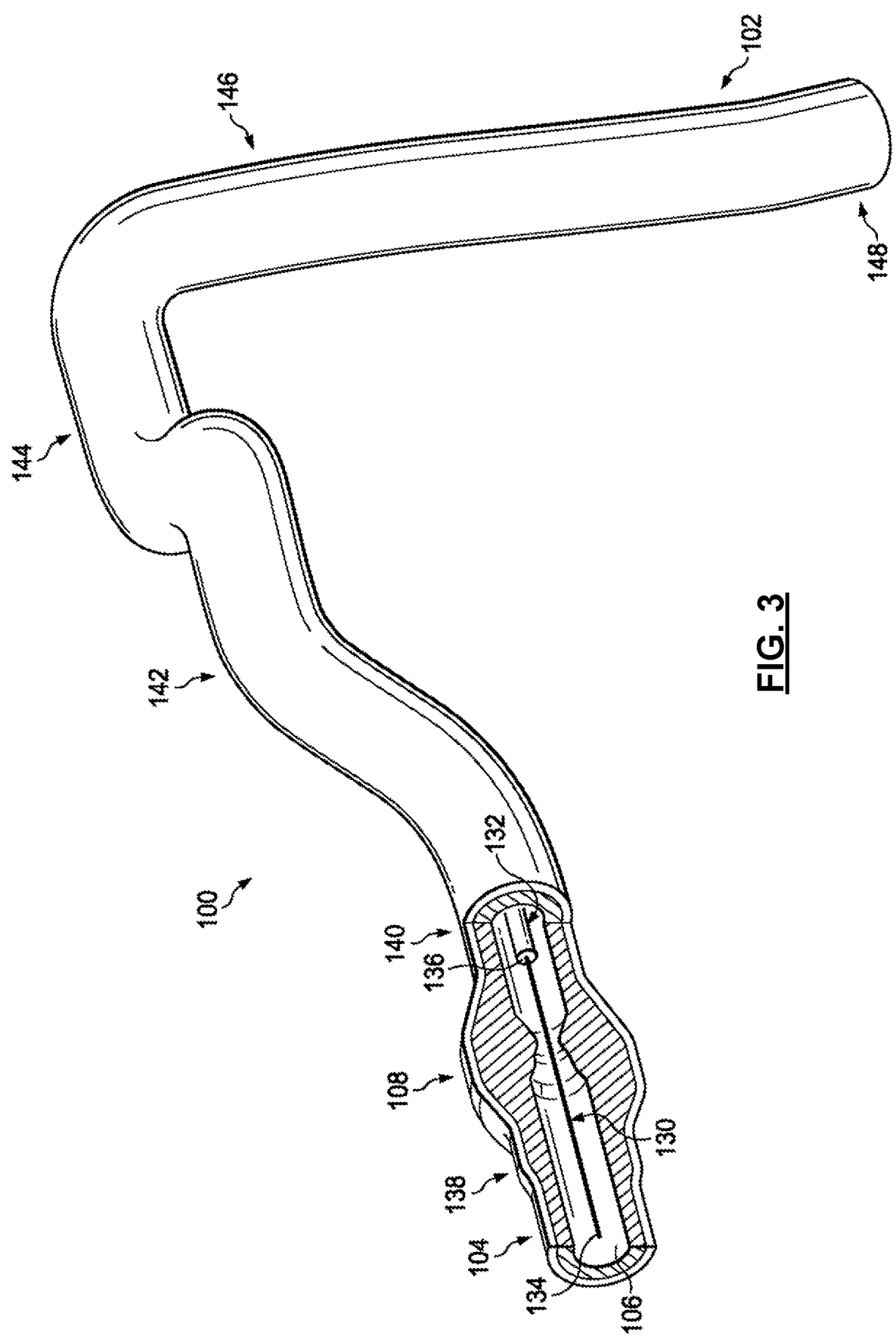
FIG. 3 is a diagrammatic, partial cross-sectional perspective view of the vessel of FIGS. 1 and 2 with instruments positioned therein according to an embodiment of the present disclosure.

Referring now to FIG. 3, the vessel 100 is shown with instruments 130 and 132 positioned therein according to an embodiment of the present disclosure. In general, instruments 130 and 132 may be any form of device, instrument, or probe sized and shaped to be positioned within a vessel. In the illustrated embodiment, instrument 130 is generally representative of a guide wire, while instrument 132 is generally representative of a catheter. In that regard, instrument 130 extends through a central lumen of instrument 132. However, in other embodiments, the instruments 130 and 132 take other forms. In that regard, the instruments 130 and 132 are of similar form in some embodiments. For example, in some instances, both instruments 130 and 132 are guide wires. In other instances, both instruments 130 and 132 are catheters. On the other hand, the instruments 130 and 132 are of different form in some embodiments, such as the illustrated embodiment, where one of the instruments is a catheter and the other is a guide wire. Further, in some instances, the instruments 130 and 132 are disposed coaxial with one another, as shown in the illustrated embodiment of FIG. 3. In other instances, one of the instruments extends through an off-center lumen of the other instrument. In yet other instances, the instruments 130 and 132 extend side-by-side. In some particular embodiments, at least one of the instruments is as a rapid-exchange device, such as a rapid-exchange catheter. In such embodiments, the other instrument is a buddy wire or other device configured to facilitate the introduction and removal of the rapid-exchange device. Further still, in other instances, instead of two separate instruments 130 and 132 a single instrument is utilized. In some embodiments, the single instrument incorporates aspects of the functionalities (e.g., data acquisition) of both instruments 130 and 132.

Instrument 130 is configured to obtain diagnostic information about the vessel 100. In that regard, the instrument 130 includes one or more sensors, transducers, and/or other monitoring elements configured to obtain the diagnostic information about the vessel. The diagnostic information includes one or more of pressure, flow (velocity), images (including images obtained using ultrasound (e.g., IVUS), OCT, and/or other imaging techniques), temperature, and/or combinations thereof. The one or more sensors, transducers, and/or other monitoring elements are positioned adjacent a distal portion of the instrument 130 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 134 of the instrument 130 in some instances. In some instances, at least one of the one or more sensors, transducers, and/or other monitoring elements is positioned at the distal tip of the instrument 130.

The instrument 130 includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Examples of commercially available guide wire products that include suitable pressure monitoring elements include, without limitation, the Verrata® pressure guide wire, the PrimeWire Prestige® PLUS pressure guide wire, and the ComboWire® XT pressure and flow guide wire, each available from Volcano Corporation, as well as the PressureWire™ Certus guide wire and the PressureWire™ Aeris guide wire, each available from St. Jude Medical, Inc. Generally, the instrument 130 is sized such that it can be positioned through the stenosis 108 without significantly impacting fluid flow across the stenosis, which would impact the distal pressure reading. Accordingly, in some instances the instrument 130 has an outer diameter of 0.018" or less. In some embodiments, the instrument 130 has an outer diameter of 0.014" or less. In other embodiments, the instrument 130 has an outer diameter of 0.035" or less.

Instrument 132 is also configured to obtain diagnostic information about the vessel 100. In some instances, instrument 132 is configured to obtain the same diagnostic information as instrument 130. In other instances, instrument 132 is configured to obtain different diagnostic information than instrument 130, which may include additional diagnostic information, less diagnostic information, and/or alternative diagnostic information. The diagnostic information obtained by instrument 132 includes one or more of pressure, flow (velocity), images (including images obtained using ultrasound (e.g., IVUS), OCT, and/or other imaging techniques), temperature, and/or combinations thereof. Instrument 132 includes one or more sensors, transducers, and/or other monitoring elements configured to obtain this diagnostic information. In that regard, the one or more sensors, transducers, and/or other monitoring elements are positioned adjacent a distal portion of the instrument 132 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 136 of the instrument 132 in some instances. In some instances, at least one of the one or more sensors, transducers, and/or other monitoring elements is positioned at the distal tip of the instrument 132.

Similar to instrument 130, instrument 132 also includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Currently available catheter products suitable for use with one or more of Siemens AXIOM Sensis, Mennen Horizon XVu, and Philips Xper IM Physiomonitoring 5 and include pressure monitoring elements can be utilized for instrument 132 in some instances.

In accordance with aspects of the present disclosure, at least one of the instruments 130 and 132 is configured to monitor a pressure within the vessel 100 distal of the stenosis 108 and at least one of the instruments 130 and 132 is configured to monitor a pressure within the vessel proximal of the stenosis. In that regard, the instruments 130, 132 are sized and shaped to allow positioning of the at least one element configured to monitor pressure within the vessel 100 to be positioned proximal and/or distal of the stenosis 108 as necessary based on the configuration of the devices. In that regard, FIG. 3 illustrates a position 138 suitable for measuring pressure distal of the stenosis 108. In that regard, the position 138 is less than 5 cm, less than 3 cm, less than 2 cm, less than 1 cm, less than 5 mm, and/or less than 2.5 mm from the distal end of the stenosis 108 (as shown in FIG. 2) in some instances. FIG. 3 also illustrates a plurality of suitable positions for measuring pressure proximal of the stenosis 108. In that regard, positions 140, 142, 144, 146, and 148 each represent a position that is suitable for monitoring the pressure proximal of the stenosis in some instances. In that regard, the positions 140, 142, 144, 146, and 148 are positioned at varying distances from the proximal end of the stenosis 108 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery.

In some embodiments, at least one of the instruments 130 and 132 is configured to monitor pressure within the vessel 100 while being moved through the lumen 106. In some instances, instrument 130 is configured to be moved through the lumen 106 and across the stenosis 108. In that regard, the instrument 130 is positioned distal of the stenosis 108 and moved proximally (i.e., pulled back) across the stenosis to a position proximal of the stenosis in some instances. In other instances, the instrument 130 is positioned proximal of the stenosis 108 and moved distally across the stenosis to a position distal of the stenosis. Movement of the instrument 130, either proximally or distally, is controlled manually by medical personnel (e.g., hand of a surgeon) in some embodiments. In other embodiments, movement of the instrument 130, either proximally or distally, is controlled automatically by a movement control device (e.g., a pullback device, such as the Trak Back® II Device available from Volcano Corporation). In that regard, the movement control device controls the movement of the instrument 130 at a selectable and known speed (e.g., 2.0 mm/s, 1.0 mm/s, 0.5 mm/s, 0.2 mm/s, etc.) in some instances.

In some embodiments, because the movement of the instrument 130 is selectable and known, the position of the distal tip 134 relative to the patient's vasculature may be estimated with sufficient precision to provide for the co-registration of data obtained by the instrument 130 with a computer model of the patient's vasculature obtained from angiography. Movement of the instrument 130 through the vessel is continuous for each pullback or push through, in some instances. In other instances, the instrument 130 is moved step-wise through the vessel (i.e., repeatedly moved a fixed amount of distance and/or a fixed amount of time). Some aspects of the visual depictions discussed below are particularly suited for embodiments where at least one of the instruments 130 and 132 is moved through the lumen 106. Further, in some particular instances, aspects of the visual depictions discussed below are particularly suited for embodiments where a single instrument is moved through the lumen 106, with or without the presence of a second instrument. In other embodiments, image-based co-registration may be performed. For example, fluoroscopy may be used to observe a visualization agent introduced into the vasculature of the patient. The tip of the instrument 130 may be used to contact a number of points within the vasculature to establish the location of those points using fluoroscopy. Additionally, radiopaque markers may be embedded in the instrument 130 to enable tracking.

In some instances, the instruments 130 and 132 may be used to provide instantaneous wave-free ratio (iFR®) measurements instead of, or in addition, to traditional FFR measurements as described above. Such iFR measurements may be obtained using products produced by the Volcano Corporation. In some embodiments, FFR data and iFR data may be used together to assess the patient. The FFR or iFR data may be used to determine whether the disease is focal or diffuse. In some embodiments, the pullback curve based on FFR or iFR may be used to determine whether the patient's disease is focal or diffuse.

Figure 4:
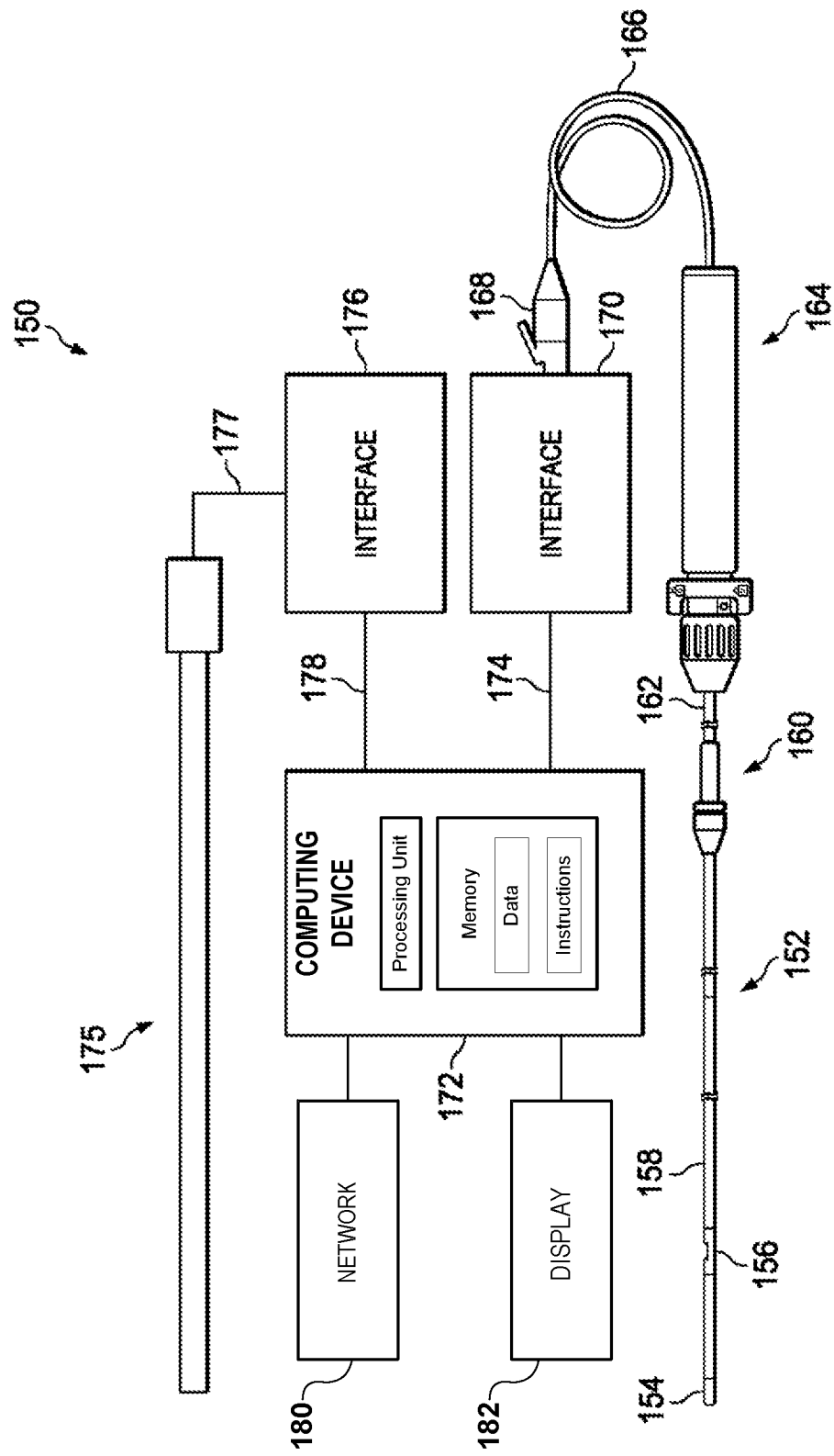
FIG. 4 is a diagrammatic, schematic view of a system according to an embodiment of the present disclosure.

Referring now to FIG. 4, shown therein is a system 150 according to an embodiment of the present disclosure. In that regard, FIG. 4 is a diagrammatic, schematic view of the system 150. As shown, the system 150 includes an instrument 152. In that regard, in some instances instrument 152 is suitable for use as at least one of instruments 130 and 132 discussed above. Accordingly, in some instances the instrument 152 includes features similar to those discussed above with respect to instruments 130 and 132 in some instances. In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. In the illustrated embodiment, the housing 156 contains at least a pressure sensor configured to monitor a pressure within a lumen in which the instrument 152 is positioned. A shaft 158 extends proximally from the housing 156. A torque device 160 is positioned over and coupled to a proximal portion of the shaft 158. A proximal end portion 162 of the instrument 152 is coupled to a connector 164. A cable 166 extends from connector 164 to a connector 168. In some instances, connector 168 is configured to be plugged into an interface 170. In that regard, interface 170 is a patient interface module (PIM) in some instances. In some instances, the cable 166 is replaced with a wireless connection. In that regard, it is understood that various communication pathways between the instrument 152 and the interface 170 may be utilized, including physical connections (including electrical, optical, and/or fluid connections), wireless connections, and/or combinations thereof.

The interface 170 is communicatively coupled to a computing device 172 via a connection 174. Computing device 172 is generally representative of any device suitable for performing the processing and analysis techniques discussed within the present disclosure. In some embodiments, the computing device 172 includes a processor, random access memory, and a storage medium. In that regard, in some particular instances the computing device 172 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer-readable medium accessible by the computing device. In some instances, the computing device 172 is a console device. In some particular instances, the computing device 172 is similar to the s5™ Imaging System or the s5i® Imaging System, each available from Volcano Corporation. In some instances, the computing device 172 is portable (e.g., handheld, on a rolling cart, etc.). Further, it is understood that in some instances the computing device 172 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

The computing device 172 may acquire data from many different sources. For example, as described herein the computing device 172 may communicate through the interface 170 to collect physiological measurements from instruments, such as instruments 130 and 132, positioned within a patient's vasculature. Additionally, the computing device 172 may include a network interface card or similar interface to communicate with a network 180. The computing device 172 may access angiography data to produce a model of the patient's vasculature or may access a pre-computed model. For example, an existing model of the patient's vasculature may have been generated based on previously acquired data. The computing device 172 may be coupled to a display 182 by which images, data, and user interfaces may be presented to a clinician before, after, and/or during a procedure.

Together, connector 164, cable 166, connector 168, interface 170, and connection 174 facilitate communication between the one or more sensors, transducers, and/or other monitoring elements of the instrument 152 and the computing device 172. However, this communication pathway is exemplary in nature and should not be considered limiting in any way. In that regard, it is understood that any communication pathway between the instrument 152 and the computing device 172 may be utilized, including physical connections (including electrical, optical, and/or fluid connections), wireless connections, and/or combinations thereof. In that regard, it is understood that the connection 174 is wireless in some instances. In some instances, the connection 174 includes a communication link over a network (e.g., intranet, internet, telecommunications network, and/or other network). For example, in some embodiments the computing device 172 may be coupled to the interface 170 by the network 180. In that regard, it is understood that the computing device 172 is positioned remote from an operating area where the instrument 152 is being used in some instances. Having the connection 174 include the connection to the network 180 can facilitate communication between the instrument 152 and the remote computing device 172 regardless of whether the computing device is in an adjacent room, an adjacent building, or in a different state/country. Further, it is understood that the communication pathway between the instrument 152 and the computing device 172 is a secure connection in some instances. Further still, it is understood that, in some instances, the data communicated over one or more portions of the communication pathway between the instrument 152 and the computing device 172 is encrypted.

The system 150 also includes an instrument 175. In that regard, in some instances instrument 175 is suitable for use as at least one of instruments 130 and 132 discussed above. Accordingly, in some instances the instrument 175 includes features similar to those discussed above with respect to instruments 130 and 132 in some instances. In the illustrated embodiment, the instrument 175 is a catheter-type device. In that regard, the instrument 175 includes one or more sensors, transducers, and/or other monitoring elements adjacent a distal portion of the instrument configured to obtain the diagnostic information about the vessel. In the illustrated embodiment, the instrument 175 includes a pressure sensor configured to monitor a pressure within a lumen in which the instrument 175 is positioned. The instrument 175 is in communication with an interface 176 via connection 177. In some instances, interface 176 is a hemodynamic monitoring system or other control device, such as Siemens AXIOM Sensis, Mennen Horizon XVu, and Philips Xper IM Physiomonitoring 5. In one particular embodiment, instrument 175 is a pressure-sensing catheter that includes fluid column extending along its length. In such an embodiment, interface 176 includes a hemostasis valve fluidly coupled to the fluid column of the catheter, a manifold fluidly coupled to the hemostasis valve, and tubing extending between the components as necessary to fluidly couple the components. In that regard, the fluid column of the catheter is in fluid communication with a pressure sensor via the valve, manifold, and tubing. In some instances, the pressure sensor is part of interface 176. In other instances, the pressure sensor is a separate component positioned between the instrument 175 and the interface 176. The interface 176 is communicatively coupled to the computing device 172 via a connection 178.

Similar to the connections between instrument 152 and the computing device 172, interface 176 and connections 177 and 178 facilitate communication between the one or more sensors, transducers, and/or other monitoring elements of the instrument 175 and the computing device 172. However, this communication pathway is exemplary in nature and should not be considered limiting in any way. In that regard, it is understood that any communication pathway between the instrument 175 and the computing device 172 may be utilized, including physical connections (including electrical, optical, and/or fluid connections), wireless connections, and/or combinations thereof, and connections through the network 180. In that regard, it is understood that the connection 178 is wireless in some instances. In some instances, the connection 178 includes a communication link over a network (e.g., intranet, internet, telecommunications network, and/or other network) like the network 180. In that regard, it is understood that the computing device 172 is positioned remote from an operating area where the instrument 175 is being used in some instances. Having the connection 178 include a connection over the network 180 can facilitate communication between the instrument 175 and the remote computing device 172 regardless of whether the computing device is in an adjacent room, an adjacent building, or in a different state/country. Further, it is understood that the communication pathway between the instrument 175 and the computing device 172 is a secure connection in some instances. Further still, it is understood that, in some instances, the data communicated over one or more portions of the communication pathway between the instrument 175 and the computing device 172 is encrypted.

It is understood that one or more components of the system 150 are not included, are implemented in a different arrangement/order, and/or are replaced with an alternative device/mechanism in other embodiments of the present disclosure. For example, in some instances, the system 150 does not include interface 170 and/or interface 176. In such instances, the connector 168 (or other similar connector in communication with instrument 152 or instrument 175) may plug into a port associated with computing device 172. Alternatively, the instruments 152, 175 may communicate wirelessly with the computing device 172. Generally speaking, the communication pathway between either or both of the instruments 152, 175 and the computing device 172 may have no intermediate nodes (i.e., a direct connection), one intermediate node between the instrument and the computing device, or a plurality of intermediate nodes between the instrument and the computing device.

Diagnostic information within a vasculature of interest can be obtained using one or more of instruments 130, 132, 152, and 175. For example, diagnostic information is obtained for one or more coronaries arteries, peripheral arteries, cerebrovascular vessels, etc. The diagnostic information can include pressure-related values, flow-related values, etc. Pressure-related values can include Pd/Pa (e.g., a ratio of the pressure distal to a lesion to the pressure proximal to the lesion), FFR (e.g. a ratio of the pressure distal to a lesion to the pressure proximal to the lesion under hyperemia), iFR (e.g., a ratio of the pressure distal to a lesion to the pressure proximal determined across the wave-free period without hyperemia), etc. Flow-related values can include coronary flow reserve or CFR (e.g., maximum increase in blood flow through the coronary arteries above the normal resting volume), basal stenosis resistance index (BSR), etc.

In some embodiments, the diagnostic information can include angiographic images and/or other two-dimensional or three-dimensional depictions of a patient's vasculature. Such angiographic images may be accessed via the network 180. For example, angiographic images of the patient's vasculature and/or associated models may be stored in a data center and accessed by the computing device 172 for use during a procedure. The diagnostic information and/or data obtained by instruments 130, 132, 152, and/or 175 are correlated or co-registered to angiographic image(s) and/or other two-dimensional or three-dimensional depictions of a patient's vasculature. Co-registration can be completed using techniques disclosed in U.S. Pat. No. 6,930,014, titled "VASCULAR IMAGE CO-REGISTRATION," which is hereby incorporated by reference in its entirety, based on the known pullback speed/distance, based on a known starting point, based on a known ending point, and/or combinations thereof. In some embodiments, diagnostic information and/or data is correlated to vessel images using techniques similar to those described in U.S. patent application Ser. No. 14/144,240, titled "DEVICES, SYSTEMS, AND METHODS FOR ASSESSMENT OF VESSELS" and filed on Dec. 30, 2013, and which claims priority to U.S. Provisional Patent Application No. 61/747,480, titled "SPATIAL CORRELATION OF INTRAVASCULAR IMAGES AND PHYSIOLOGICAL FEATURES" and filed Dec. 31, 2012, which are hereby incorporated by reference in their entirety. In some embodiments, co-registration and/or correlation can be completed as described in U.S. patent application Ser. No. 14/335,603, titled "DEVICES, SYSTEMS, AND METHODS FOR ASSESSMENT OF VESSELS" and filed on Jul. 19, 2013, and which claims priority to U.S. Provisional Patent Application No. 61/856,509, titled "DEVICES, SYSTEMS, AND METHODS FOR ASSESSMENT OF VESSELS" and filed Jul. 19, 2013, which are hereby incorporated by reference in their entirety.

Figure 5:
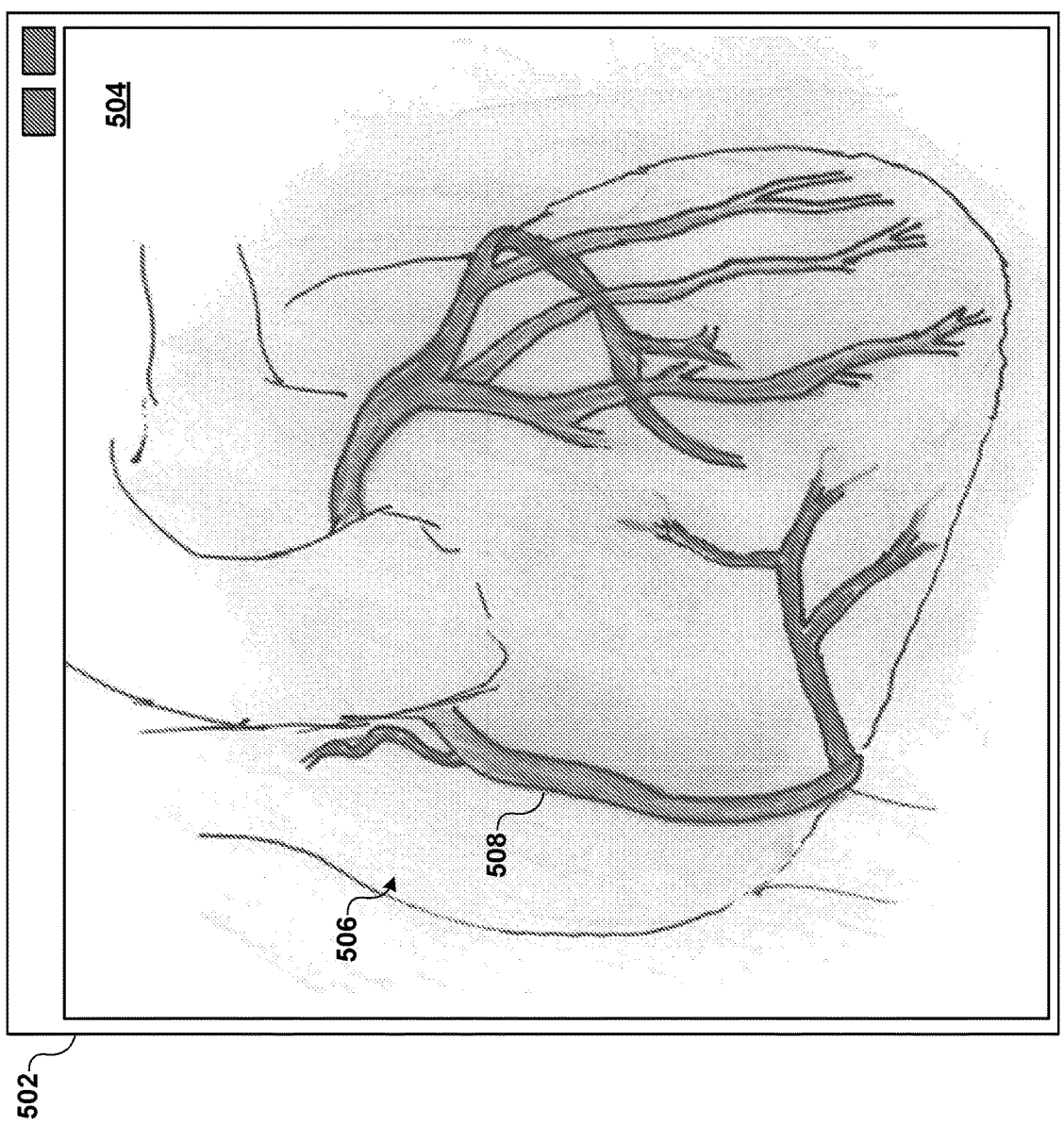
FIG. 5 is a stylized image of a patient's vasculature as seen in an angiogram image according to an embodiment of the present disclosure.

Referring now to FIG. 5, shown therein is an exemplary depiction of angiogram data as may be provided to the clinician in a user interface 500, such as may be provided by the computing device 172 of FIG. 4. Other embodiments, of the present disclosure may be other imaging modalities, such as magnetic resonance imaging (MRI), computed tomography (CT), etc. The user interface 500 includes a window 502 that may be presented in the display 182 as seen in FIG. 4. The window displays angiogram data that includes cardiac tissue 506 and vasculature 508 obtained using a contrast agent. In some embodiments, the window displays CT data. In some embodiments, the angiogram 504 may be a three-dimensional angiogram that may be manipulated by the clinician to provide different views, including different perspective views and/or cross-sectional views, of the patient's vasculature. During subsequent procedures, the clinician may navigate the instruments 130 and/or 132 through the patient's vasculature, collecting physiologic measurements therein. The physiologic measurements may be stored in a memory of the computing device 172 and also displayed on the display 182. The image-based physiologic measurements may include a dominance classification, a degree of occlusion of a lesion, which may be expressed as a percent diameter stenosis, a classification of a lesion, a degree of bending of a vessel of the vessel system, a length of a lesion, and/or a degree of calcification of a lesion.

After obtaining the angiogram data, the data may be parsed by an image-processing component provided by the system 150 of FIG. 4 to segment the patient's vasculature and estimate certain features thereof. The parsing of the data may be performed to extract image-based physiologic measurements that may be provided to a risk calculator to generate a disease quantification score. This disease quantification score may be automatically performed, without the continued interaction of a clinician. For example, the image-based physiologic measurements may be extracted after an angiogram collection process is complete. Examples of risk calculators that may be used to generate the disease quantification score are provided below.

When processing the angiogram data, quantitative coronary angiography (QCA) may be used to assess and identify blockages from the image-based data. A QCA process may be initiated automatically to identify any blockages. While the clinician may provide a qualitative evaluation based on his or her own experience, the information from the QCA process may be used in subsequent steps to automatically generate an objective intervention recommendation. As is discussed in further detail below, co-registration techniques incorporated herein by reference and others that may be known to those of skill in the art may be used to co-register physiologic measurements to specific positions in a model of the patient's vasculature 508 generated from the angiogram 504 presented in the window 502.

Figure 6:
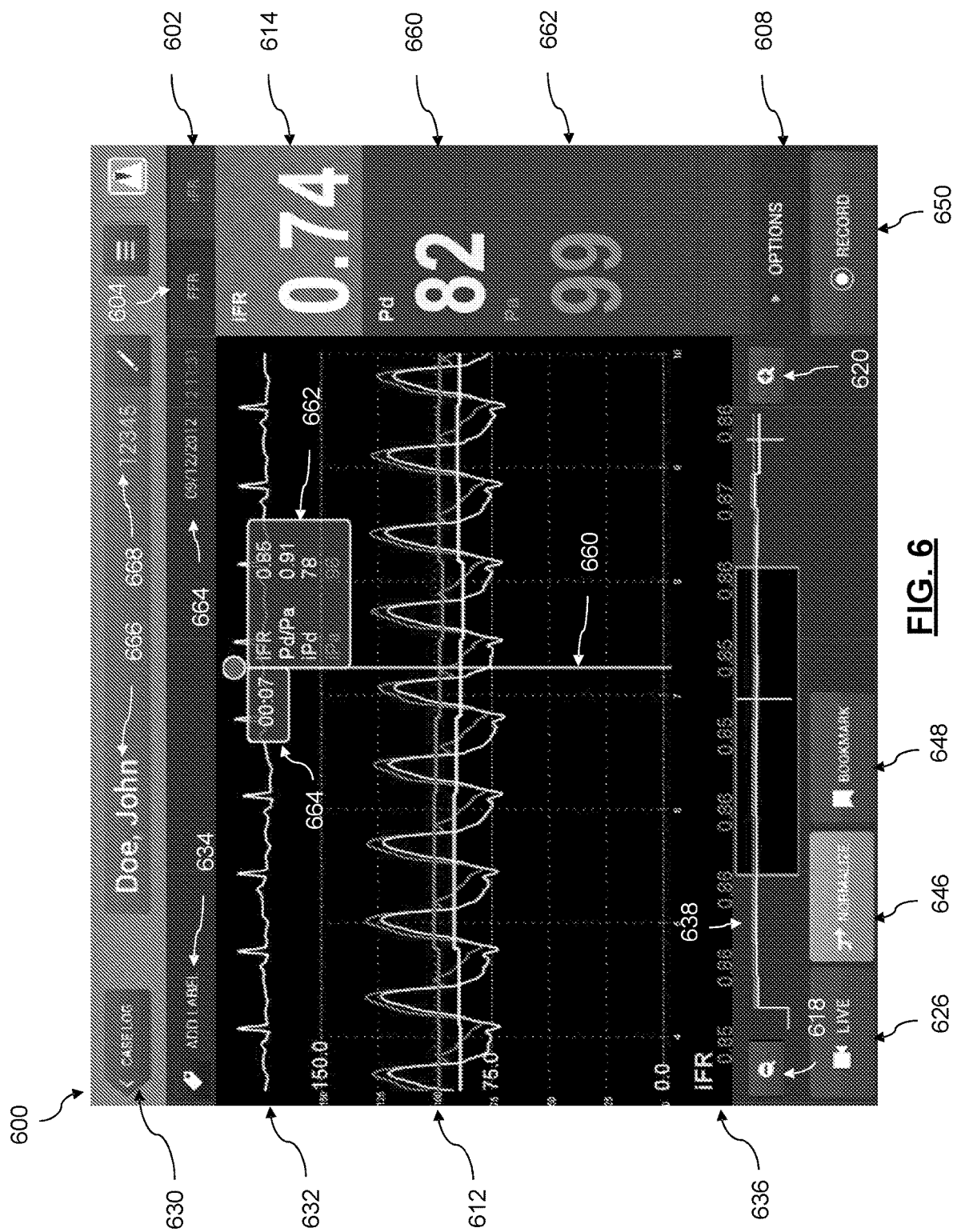
FIG. 6 is an annotated version of a user interface according to an embodiment of the present disclosure.

Referring now to FIG. 6, shown therein is a depiction of a user interface 600 for evaluating a vessel based on obtained physiologic measurements (as depicted, pressure measurements, but may also include flow volume, flow velocity, tissue characterization, and/or other intravascular physiologic measurements or calculations based thereon) according to embodiments of the present disclosure. The user interface may be displayed on a touch-sensitive display. A clinician can view, analyze, and interact with the pressure data and/or visual representations of the pressure data. As illustrated, the user interface 600 is associated with a pressure ratio workflow, but other embodiments of the user interface 600 may be associated with other modalities. The user interface 600 includes an FFR tab 604 and an iFR tab 602. The iFR tab 602 can include the obtained pressure measurements, and visual representations of the pressure measurements. As shown, the iFR tab 602 includes pressure waveform plots 612 and 638, both of which illustrate acquired pressure data over the same time period. The user interface 600 also includes a window 614 that shows a calculated pressure ratio (e.g., FFR, iFR, or otherwise).

In that regard, the pressure waveform plots 612 and 638 and the calculated pressure ratio of user interface 600 illustrate aspects of pressure measurements obtained as one instrument is moved through the vessel and another instrument is maintained at a fixed location. In that regard, in some instances the pressure measurements are representative of a pressure ratio between a fixed location within the vessel and the moving position of the instrument as the instrument is moved through the vessel. For example, in some instances a proximal pressure measurement is obtained at a fixed location within the vessel while the instrument is pulled back through the vessel from a first position distal of the position where the proximal pressure measurement is obtained to a second position more proximal than the first position (i.e., closer to the fixed position of the proximal pressure measurement).

For clarity in understanding the concepts of the present disclosure, this arrangement will be utilized to describe many of the embodiments of the present disclosure. However, it is understood that the concepts are equally applicable to other arrangements. For example, in some instances, the instrument is pushed through the vessel from a first position distal of the proximal pressure measurement location to a second position further distal (i.e., further away from the fixed position of the proximal pressure measurement). In other instances, a distal pressure measurement is obtained at a fixed location within the vessel and the instrument is pulled back through the vessel from a first position proximal of the fixed location of the distal pressure measurement to a second position more proximal than the first position (i.e., further away from the fixed position of the distal pressure measurement). In still other instances, a distal pressure measurement is obtained at a fixed location within the vessel and the instrument is pushed through the vessel from a first position proximal of the fixed location of the distal pressure measurement to a second position less proximal than the first position (i.e., closer the fixed position of the distal pressure measurement).

The pressure differential between the two pressure measurements within the vessel (e.g., a fixed location pressure measurement and a moving pressure measurement) is calculated as a ratio of the two pressure measurements (e.g., the moving pressure measurement divided by the fixed location pressure measurement), in some instances.

The visual representations in the user interface 600 can illustrate the pressure ratio and/or the underlying pressure measurements in any suitable way. Generally speaking, the representation of the data can be utilized to identify gradients/changes in the pressure ratio and/or the underlying pressure measurements that can be indicative of a significant lesion in the vessel. In that regard, the visual representation of the data can include the pressure measurement(s); a ratio of the pressure measurements; a difference in the pressure measurements; a gradient of the pressure measurement(s), the ratio of the pressure measurements, and/or the difference in the pressure measurements; first or second derivatives of the pressure measurement(s), the ratio of the pressure measurements, and/or the difference in the pressure measurements; and/or combinations thereof.

For example, the pressure waveform plots 612 and 638 show corresponding pressure data. In that regard, the pressure waveform plots 612 and 638 can include the pressure waveform for the pressure sensing device moved through the vessel during the pullback, the pressure waveform for the stationary pressure sensing device, or both. In the illustrated embodiment, the pressure waveform plots 612 and 638 include the pressure waveforms for both. In some instances the pressure waveform plot 612 is augmented to highlight or otherwise accentuate the pressure data corresponding to the diagnostic window utilized for the pressure ratio calculations.

The pressure waveform plots 612 and 638 include time on the x-axis and magnitude of pressure on the y-axis. The pressure waveform plot 638 illustrates the obtained pressure measurements over a greater amount of time compared to the waveform plot 612. For example, the pressure waveform plot 638 illustrates the entire acquisition, pullback, or "run" while the pressure waveform 612 illustrates at least a portion thereof. As shown in FIG. 6, a user provides a touch input near seven seconds on the pressure waveform plot 612. In response to the user touch input, the user interface 600 can be modified to include one or more information overlays 660, 662, and/or 664. The overlay 660 is a vertical line highlighting the time selected by the user by the touch input. The overlay 660 can be variously colored to visually distinguish the selected time. The overlay 664 provides the numerical value of the time that is selected by the user touch input. The overlay 662 provides pressure data at the selected time. In that regard, the overlay 662 can include a numerical value of a calculated pressure ratio (iFR, FFR, etc.) at the selected time, a numerical value of a compensated Pd/Pa at the selected time, a numerical value of the average Pd value at the selected time, a numerical value of the average Pa value at the selected time, a numerical value of the actual Pd value at the selected time, and/or a numerical value of the actual Pd value at the selected time. The numerical values in the overlay 662 can be raw or modified values. When a particular time is highlighted in response to a user touch input in the pressure waveform plot 612, the user interface 600 can be automatically modified to include a corresponding overlay of the curve 642 in the pressure waveform plot 638 to contextualize the highlighted time within the entire acquisition. The user interface 600 also provides pressure ratios 636 (e.g., iFR, compensated Pa/Pd values, etc.) at fixed intervals. For example, in FIG. 6, the iFR values 636 for each heartbeat cycle are displayed below the pressure waveform plot 612. In other embodiments, the pressure ratios are displayed at various locations relative to the pressure waveform plot 612.

The user interface 600 also includes a window 614 that shows a calculated pressure ratio (e.g., FFR, iFR, or otherwise). In the illustrated embodiment of FIG. 6, the window 614 shows an iFR pressure ratio value during a pullback. As shown in FIG. 6, the user interface 600 provided on the display 182 includes a button 626 to allow a clinician to go back to a "Live" mode (or to toggle between a "Live" mode and a "Review" mode), in which the user interface 600, including pressure waveform plots 612 and 638, calculated pressure ratios 636, and/or the windows 614, 670, 672 are updated in real time as a procedure is being performed. The record button 650 can be selected by a user touch input on the bedside controller to begin storing the acquired pressure data. When the user interface 600 is presented in "Review" mode, as shown in FIG. 6, the user interface 600 shows data obtained previously. With respect to the "Live" mode, it should be noted that the determination of the diagnostic window and/or the calculation of the pressure differential are performed in approximately real time or live to identify the diagnostic window of the heartbeat cycle and calculate the pressure differential. In that regard, calculating the pressure differential in "real time" or "live" within the context of the present disclosure is understood to encompass calculations that occur within 10 seconds of data acquisition. It is recognized, however, that often "real time" or "live" calculations are performed within 1 second of data acquisition. In some instances, the "real time" or "live" calculations are performed concurrent with data acquisition. In some instances the calculations are performed by a processor in the delays between data acquisitions. For example, if data is acquired from the pressure sensing devices for 1 ms every 5 ms, then in the 4 ms between data acquisitions the processor can perform the calculations. It is understood that these timings are for example only and that data acquisition rates, processing times, and/or other parameters surrounding the calculations will vary. In other embodiments, the pressure differential calculation is performed 10 or more seconds after data acquisition. For example, in some embodiments, the data utilized to identify the diagnostic window and/or calculate the pressure differential are stored for later analysis.

By comparing the calculated pressure differential to a threshold or predetermined value, a physician or other treating medical personnel can determine what, if any, treatment should be administered. In that regard, in some instances, a calculated pressure differential above a threshold value (e.g., 0.80 on a scale of 0.00 to 1.00) is indicative of a first treatment mode (e.g., no treatment, drug therapy, etc.), while a calculated pressure differential below the threshold value is indicative of a second, more invasive treatment mode (e.g., angioplasty, stent, etc.). In some instances, the threshold value is a fixed, preset value. In other instances, the threshold value is selected for a particular patient and/or a particular stenosis of a patient. In that regard, the threshold value for a particular patient may be based on one or more of empirical data, patient characteristics, patient history, physician preference, available treatment options, and/or other parameters.

In that regard, the coloring and/or other visually distinguishing aspect of the pressure differential measurements depicted in pressure ratios 636 and/or window 614 of the user interface 600 of FIG. 6 are configured based on the threshold value in some instances. For example, a first color (e.g., green, white, or otherwise) can be utilized to represent values well above the threshold value (e.g., where the threshold value is 0.80 on a scale of 0.00 to 1.00, values above 0.90), a second color (e.g., yellow, gray, or otherwise) can be utilized to represent values near but above the threshold value (e.g., where the threshold value is 0.80 on a scale of 0.00 to 1.00, values between 0.80 and 0.90), and a third color (e.g., red, black, or otherwise) can be utilized to represent values equal to or below the threshold value (e.g., where the threshold value is below 0.80 on a scale of 0.00 to 1.00, values of below 0.80). It is appreciated that any number of color combinations, scalings, categories, and/or other characteristics can be utilized to visually represent the relative value of the pressure differential to the threshold value. However, for the sake of brevity Applicants will not explicitly describe the numerous variations herein.

The user interface 600 includes an ECG waveform 632. The user interface 600 additionally may include a patient name 666, patient identifier 668, and a date/time 674. The case log button 600 can be selected access additional information about the patient (e.g., other pressure acquisitions) and/or retrieve the current pressure acquisition data at a later time. A label field 634 allows the user to input additional notes regarding the patient or the procedure. Selecting the label field 634 by a touch input on the system can cause an on-screen keyboard to be displayed in the display 182. Other means of input, such as a mouse, a keyboard, voice-control, etc. may be used in other embodiments.

In obtaining physiology data, whether pressure or flow, etc. the data may be obtained at regular intervals and displayed in the user interface 600 according to those regular intervals. For example, each of the data samples indicated by the lines in FIG. 6 may be obtained during a pullback. When the rate of the pullback is known, a location of each data point may be co-registered with a specific location within the patient's vasculature. Accordingly, physiologic measurements that are collected using the instruments 130 and 132 may be associated with specific locations within the patient's vasculature. While the example of pressure measurements is used often herein, in some embodiments, other physiology measurement data and/or imaging data may be collected and co-registered. For example, IVUS data may be collected and processed to identify calcium deposits or plaques. Like pressure and/or flow data, this other information may be co-registered with the angiogram data such that the location of the calcium deposits may be depicted in connection with a model of the patient's vasculature in the display 182.

Figure 7:
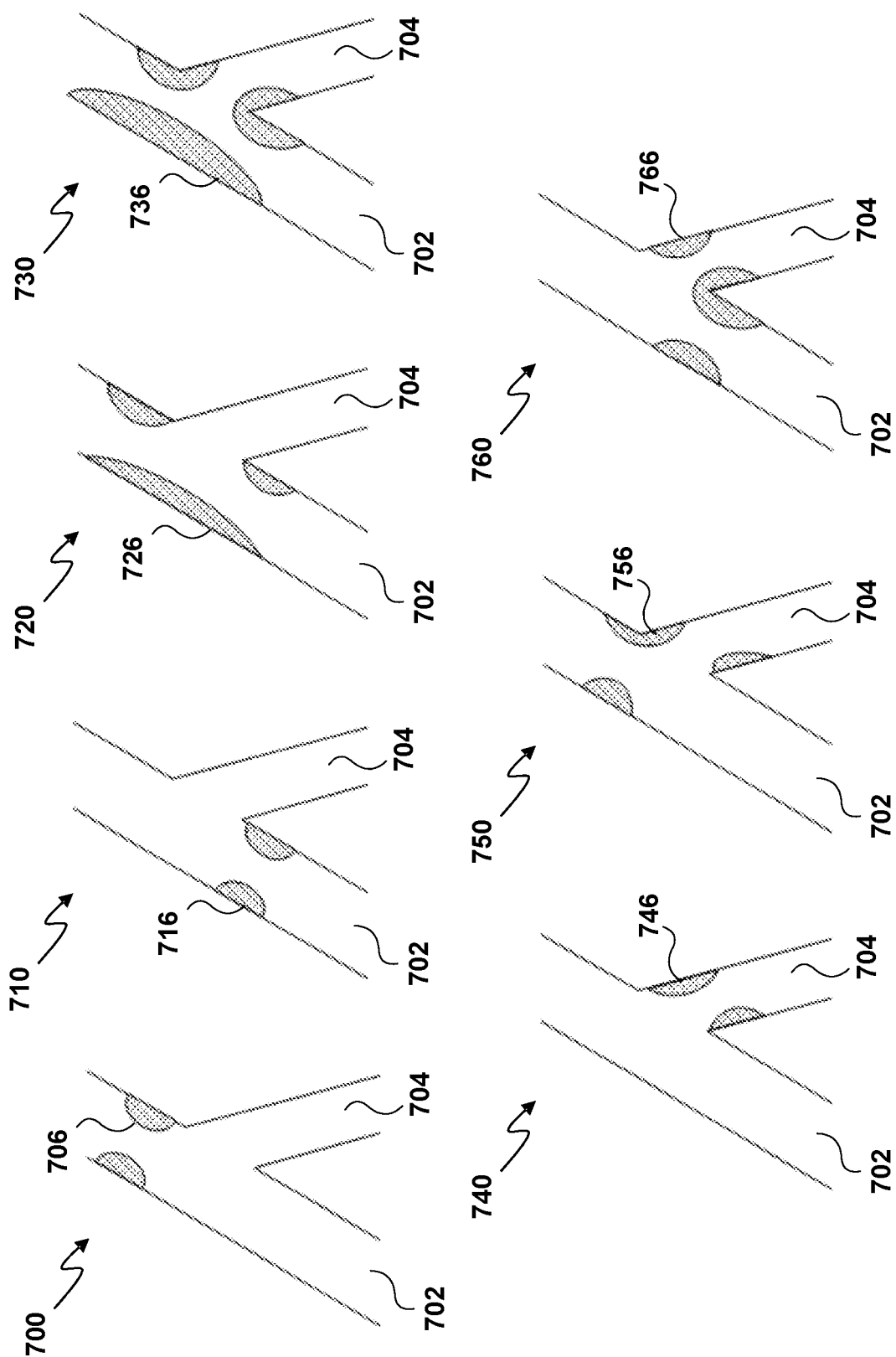
FIG. 7 is a series of stylized images of a vessel illustrating classification of vessel obstructions according to an embodiment of the present disclosure.

Referring now to FIG. 7, shown therein is a plurality of bifurcation lesions that may be detected and classified using imaging data, such as may be provided by IVUS inspection. The imaging data may include an indication of whether an imaged surface is tissue, plaque, or a calcium deposit. The bifurcation 700 includes a main vessel 702 and a side vessel 704, and includes a stenosis 706 within the main vessel 702 only and positioned before the branching of the side vessel 704. The bifurcation 710 depicts a stenosis 716 positioned within the main vessel 702 only and after the branching of the side vessel 704. Bifurcation 720 includes a stenosis 726 situated adjacent to the branching of the side vessel 704, but limited to the main vessel 702. The stenosis 726 includes portions both before and after the branching of the side vessel 704 the bifurcation 730 includes a stenosis 736 that is situated adjacent to the branching of the side vessel 704, similar to the stenosis 726. However, the stenosis 736 includes portions within the side vessel 704. The bifurcation 740 includes a stenosis 746 situated within the side vessel 704 only. The bifurcation 750 includes a stenosis 756 adjacent to the branching and including a portion before the branching in the main vessel 702 and a portion after the branching in the side vessel 704. The bifurcation 760 depicts a stenosis 766 having portions proximate the branching and after the branching in both the main vessel 702 and the side vessel 704. Using IVUS data or other suitable data, the system 150 may perform image-processing and image-recognition to classify lesions occurring in each of the segments of interests. The segments may be labeled with the conventional names for each of the segments. Information regarding the segments, including classifications and associated severities, may be provided to a risk calculator.

The risk calculator, whether a SYNTAX score calculator or another disease quantification score calculator, may then provide a disease quantification score. When the disease quantification score is above a threshold, the system 150 may recommend a CABG surgery is the appropriate intervention. When the disease quantification score is below the threshold the system 150 may recommend PCI. While risk calculators, such as the SYNTAX score calculator, have been available to clinicians previously, the system 150 provides for the automatic calculation and determination of the SYNTAX score or other such disease quantification score. Accordingly, the disease quantification score may be displayed to the clinician during an assessment procedure.

Figure 8A:
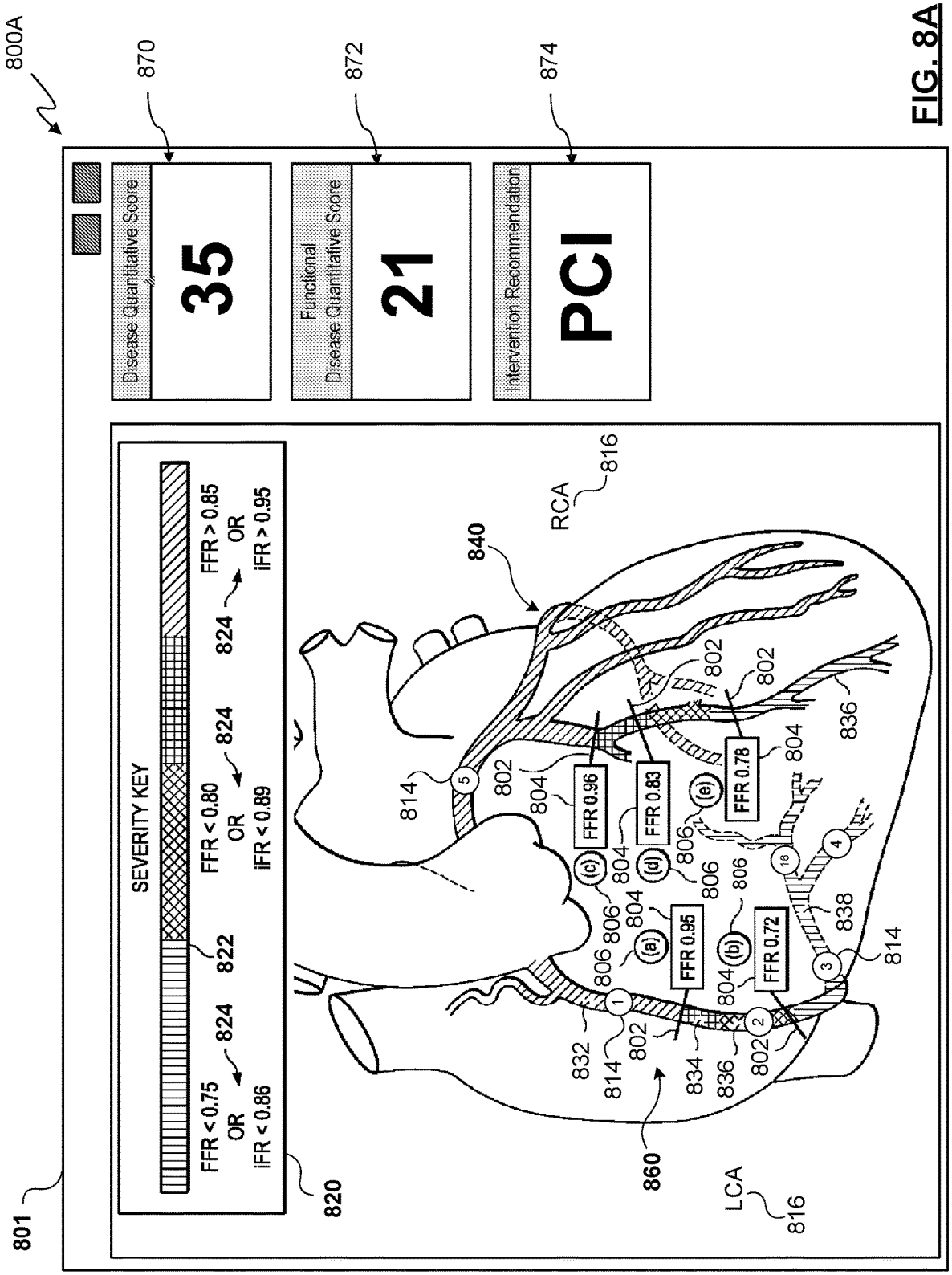
FIG. 8A is a stylized image of a patient's vasculature as seen in a user interface according to an embodiment of the present disclosure.

Referring now to FIG. 8A, shown therein is an annotated depiction of stylized images of a vessel according to embodiments of the present disclosure. The stylized user interface 800A of FIG. 8A may be presented to a clinician in a display, as a window 801, and incorporates angiogram data with an overlay of co-registered physiologic measurements as described herein. As described herein, the physiologic measurements collected using pressure sensors or other sensors may be co-registered with the angiogram data or, in some embodiments, with a two-dimensional or three-dimensional model prepared therefrom. In other embodiments, angiogram data and the co-registered physiologic measurements may be presented separately and not overlaid as illustrated. FIG. 8A includes stylized images 840 and 860 of the right coronary artery and of the left coronary artery, respectively. FIG. 8A further includes an index 820 for assessing the severity of one or more lesions and/or stenoses according to an embodiment of the present disclosure. FIG. 8A can be displayed on a display 182 of system 150 for assessing a patient's vasculature. That is, one or more components (e.g., a processor and/or processing circuit) of the system can render information, including angiogram data and physiologic measurements, to provide display data to cause the display of the images shown in FIG. 8A. In some embodiments, the representations of the LCA 860 and the RCA 840 may be further stylized and/or presented without the underlying angiogram data.

The images of the stylized vessels in FIG. 8A are annotated with one or more visualizations configured to assist in identifying one or more lesions and/or stenoses, and/or assess the severity thereof. These annotations may be automatically provided by performing image-recognition on angiogram data and/or other data, such as IVUS imaging data. The visualizations are based on physiology values obtained from one or more instruments (e.g., instruments 130 and/or 132) as at least one of the instruments is moved through the vessel. The stylized vessels of FIG. 8A can be colorized and/or otherwise visualized using a heat map that illustrates changes in pressure measurements (or other physiologic measurements, such as flow volume, flow velocity, etc.) obtained as the instrument is moved through the vessel. Hatchings are used in FIG. 8A to represent such visualizations. In that regard, in some instances the pressure measurements shown in the heat map are representative of a pressure differential between a fixed location within the vessel and the moving position of the instrument as the instrument is moved through the vessel. For example, in some instances a proximal pressure measurement is obtained at a fixed location within the vessel while the instrument is pulled back through the vessel from a first position distal of the position where the proximal pressure measurement is obtained to a second position more proximal than the first position (i.e., closer the fixed position of the distal pressure measurement), such as is discussed herein in connection with FIG. 6. Accordingly, FIG. 8A includes depictions of co-registered physiologic measurements.

By comparing the calculated pressure differential to a threshold or predetermined value, a clinician or other treating medical personnel can determine what, if any, treatment should be administered. In that regard, in some instances, a calculated pressure differential above a threshold value (e.g., 0.80 on a scale of 0.00 to 1.00) is indicative of a first treatment mode (e.g., no treatment, drug therapy, etc.), while a calculated pressure differential below the threshold value is indicative of a second, more invasive treatment mode (e.g., angioplasty, stent, etc.). In some instances, the threshold value is a fixed, preset value. In other instances, the threshold value is selected for a particular patient and/or a particular stenosis of a patient. In that regard, the threshold value for a particular patient may be based on one or more of empirical data, patient characteristics, patient history, physician preference, available treatment options, and/or other parameters.

In that regard, the coloring and/or other visually distinguishing aspect of the physiology values (e.g., pressure differential measurements) depicted in FIG. 8 are configured based on the threshold value. The severity key or index 820 shows the colors 822 and their corresponding physiological values 824. For example, a first color (e.g., green, medium grey, or otherwise) is utilized to represent values well above the threshold value (e.g., where the threshold value is 0.80 on a scale of 0.00 to 1.00, values above 0.85), a second color (e.g., yellow, white, or otherwise) is utilized to represent values near but above the threshold value (e.g., where the threshold value is 0.80 on a scale of 0.00 to 1.00, values between 0.82 and 0.84), a third color (e.g., orange, light grey, or otherwise) is utilized to represent values near the threshold value (e.g., where the threshold value is 0.80 on a scale of 0.00 to 1.00, values between 0.79 and 0.81), and a fourth color (e.g., red, dark grey, or otherwise) is utilized to represent values equal to or below the threshold value (e.g., where the threshold value is 0.80 on a scale of 0.00 to 1.00, values of 0.79 and below).

Area 832 of FIG. 8A indicates parts of the vessel with low severity (e.g., areas with a relatively high FFR value). Area 834 indicates parts of the vessel with greater severity compared to area 832 (e.g., areas with a moderately high FFR value). Area 836 indicates parts of the vessel with a moderate severity (e.g., areas with a moderately low FFR value). Area 838 indicates parts of the vessel with a high severity (e.g., areas with a low FFR value). It is appreciated that any number of color combinations, scalings, categories, and/or other characteristics can be utilized to visually represent the relative value of the pressure differential to the threshold value. However, for the sake of brevity Applicants will not explicitly describe the numerous variations herein.

In some embodiments, the heat map included in FIG. 8A is based on a cumulative or total pressure differential, where the color selected for a particular point is determined based on the pressure differential between the instrument at that point being moved through the vessel and the stationary or fixed instrument. In other embodiments, the heat map is based on localized pressure differential, where the color selected for a particular point is determined based on differences between the pressure differential of that point with one or more of the surrounding points. In that regard, the localized pressure differential is calculated as the difference between the immediately preceding point in some instances. For example, the localized pressure differential for point $P_n$ is equal to the cumulative or total pressure differential for point $P_n$ minus the total or cumulative pressure differential for point $P_{n-1}$. In other instances, the localized pressure differential is calculated as the difference between that point and a point a fixed amount of time (e.g., 10 ms, 5 ms, 2 ms, 1 ms, or otherwise) or distance (e.g., 10 mm, 5 mm, 2 mm, 1 mm, or otherwise) away from that point. By utilizing a localized pressure differential the location of significant changes in pressure differential values, which are often associated with the presence of a lesion or stenosis, can be identified.

FIG. 8A includes transition points or areas of the vessel wherein the physiology values between portions of the vessel change by a threshold amount. In some embodiments, the threshold amount can be fixed, while in other embodiments, the threshold amount can vary between patients. The one or more transition points can be indicated by visualizations. In FIG. 8A, the visualizations are markers 802. Markers 802 can be described as tick marks. In some embodiments, markers 802 can extend transversely across the vessel. In other embodiments, markers 802 can take different shapes (e.g., circles, squares, etc.), be in different positions relative to the vessel (beside, within, etc.), be differently sized, etc. The transition points can be representative of a boundary of a lesion or stenosis of the vessel that results in an increased or decreased pressure differential, which is illustrated by the change in color of the vessel. As a result, one or more visualizations (e.g., the change in color, markers 802, etc.) can be utilized to both identify the location of the lesion or stenosis within the vessel and assess the severity of the lesion or stenosis. For example, under some conditions, the angiogram data may appear to show a normal vessel, while the physiologic measurements presented in the heat map (and shown overlaid on the angiogram data in the user interface 800A) may provide additional information. Similarly, while the angiogram data may provide a basis for a disease quantification score, the incorporation of the physiologic measurements obtained within the vessels provides a broader basis for the functional disease quantification score.

FIG. 8A includes visualizations for providing diagnostic information collected by one or more instruments at a corresponding location of the vessel on the display. In that regard, value indicators 804 can be disposed adjacent to markers 802 to indicate the location within the patient's vasculature to which the measurement corresponds. In other embodiments, value indicators 804 are displayed further away from markers 802, but an additional visual element (e.g., an arrow, a straight line, a curved line, marker 802 and value indicator 804 are the same or similar colors, etc.) is provided to indicate the location of the measurement. In some embodiments, the value indicators 804 include only the value of the physiological measurement (e.g., "0.96"), while in other embodiments, the value indicators 804 include the value and type of physiological measurement (e.g., "0.95 FFR"). In yet other embodiments, additional information, such as the time the measurement was taken, severity of the stenosis or lesion, etc. can also be provided. For example, a user may provide a user input (e.g., a selection from a drop-down menu, toggle through the available options, etc.) selecting the types of information that should be displayed in value indicators 804. Labels 806, for each of the value indicators 804, can also be provided. Labels 806 can include alphabetical, numeric, and/or other symbolic characters. Labels 806 may assist in identifying markers 802 and/or value indicators 804 (e.g., to distinguish between different markings/value indicators and/or to facilitate discussion of the vessel depictions).

In some embodiments, markers 802 and/or value indicators 804 can be positioned automatically based on the physiologic measurements. The system can be configured to select locations within the vessel that are clinically significant based on the diagnostic information (e.g., locations where the physiologic measurements change significantly, such as points at which pressure changes). Similarly, the one or more visualizations of FIG. 8A can include labels 814 and/or labels 816 for various predefined segments of the patient's vasculature. These labels 814 and 816 may also be automatically generated based on the angiogram data using image-recognition and modeling techniques. Labels 816 can be textual indications providing the names of major and/or minor vessels or segments thereof. Labels 814 can include alphabetical, numeric, and/or other symbolic characters. In some embodiments, labels 814 can correspond to a listing of parts of patient's vasculature. For example, labels 814 can be based on parts of the patient's vasculature as identified according to one or more risk calculators. The segments identified by labels 814 and/or 816 include, but are not limited to, right coronary artery (RCA), left main coronary artery, circumflex coronary artery, left anterior descending (LAD), RCA proximal, RCA mid, RCA distal, LAD proximal, LAD mid, LAD apical, first diagonal, additional first diagonal, second diagonal, additional second diagonal, proximal circumflex, intermediate/anterolateral, obtuse marginal, distal circumflex, left posterolateral, posterior descending, among others. In some embodiments, the labels 814 and 816 are included automatically by the system 150 upon performing an image-recognition process on the angiogram information such as that depicted in the user interface 500 of FIG. 5. The angiogram information may include, information characterizing or describing features of the vessel system such as the contours, location, branches, and other features of the vessel(s) to automatically identify individual vessels within the patient's vasculature. In this way, a model of the patient's vasculature may be generated and parsed to identify specific sections warranting the appropriate label. While abbreviations and particular vessels are used in FIG. 8A, it is understood that any suitable label can be used.

These labels 814 and 816 may also be used by the system 150 in generating a disease quantification score. For example, the disease quantification score may be a SYNTAX score such as that described in Georgios Sianos, et al., *The SYNTAX Score: and angiographic tool grading the complexity of coronary artery disease*, EuroIntervention; v. 2005; 1:219-227, which is incorporated by reference herein in its entirety. For example, where the patient's vasculature being observed is the patient's coronary tree, the system 150 may parse angiographic data to identify segments that may then be analyzed individually to collect data and insert into a risk calculator such as that available at www.syntaxscore.com, that operates on segment-specific data. In various embodiments, the risk calculator can include one or more algorithms for calculating the likelihood of mortality, the likelihood of success when treating the lesion or stenosis, etc. The disease quantification score may be based on the provided data and any additional relevant patient history. The provided data and/or patient history can include binary (e.g., yes or no) and/or continuous (e.g., percentage of narrowing of the vessel) values. The provided data may be based on measured diagnostic information. The provided data can include one or more of existence of mitral stenosis, existence of aortic stenosis, existence of total occlusion, existence of trifurcation and how many diseased segments involved, existence of bifurcation, existence of aorto ostial lesion, existence of severe tortuosity in the vessel, whether length of the lesion is greater than 20 mm or another length, existence of heavy calcification, existence of thrombus, if and which segments are diffusely diseased and/or narrowed, number of lesions, percentage of narrowing, involvement of proximal LAD lesion, etc. Other relevant patient history can include one or more of age; gender; whether the patient has diabetes, hypertension, hypercholesterolemia, peripheral vascular disease; whether the patient is currently smoking; whether the patient has a positive family history of heart disease; whether the patient has had a previous myocardial infarction and/or previous PCI; the ventricular ejection fraction percentage, etc. The risk calculator may output a quantity that is an objective measure of the risk associated with the patient's condition based upon the provided imaging data, non-invasive physiologic measurements, and patient history.

Some embodiments of the risk calculator may include a fractional flow reserve (FFR)-guided SYNTAX score (SS) or functional SYNTAX score (FSS), as described in Chang-Wook Nam, et al., *Functional SYNTAX Score for Risk Assessment in Multivessel Coronary Artery Disease*, Journal of the American College of Cardiology 2011; 58(12): 1211-1218, which is incorporated by reference herein in its entirety. As used herein, the "functional SYNTAX score" includes SYNTAX scores that incorporate FFR data, iFR, and/or other types of physiology measurement data. In calculating the disease quantification score, information may be obtained from externally obtained images, such as angiogram data and from previously obtained patient health information, including previously performed examinations. In using the risk calculator to determine the disease quantification score, obstructions in the labeled segments (labeled with the labels 814) may be analyzed for classification and for assessment of severity.

The user interface 800A may further include a disease quantification score window 870 that communicates the patient's disease quantification score to the clinician. Additionally, a functional disease quantification score is also presented in a functional disease quantification score window 872. This functional disease quantification score may be derived using the co-registered physiologic measurements to further inform the disease quantification score. Such co-registered physiologic measurements may include measurements such as FFR and/or iFR measurements. The co-registered physiologic measurements may be used to adjust the inputs to the risk calculator. For example, when the physiologic measurements indicate that a lesion automatically detected from the angiogram data causes an insignificant pressure drop within the vasculature, a factor may be added to the inputs to the risk calculator to more appropriately weigh the corresponding lesion. For example, as shown in the window 801, pressure drops are observed between point A and point B, between points C and D, and between points D and E. Each of these pressure drops may be associated with a specific lesion that may be identified from visual data, such as externally obtained angiogram data and/or internally obtained IVUS data. While the visual data may provide sufficient information to obtain a disease quantification score, the physiology data may indicate the relative significance of each identified lesion. For example, the drop caused by a lesion between points D and E may be indicated as less significant by the physiologic measurements. Accordingly, data entered into the risk calculator that is associated with the lesion between points D and E may be given less weight by the addition of a mitigating factor.

As shown in the functional disease quantification score window 872, this mitigating factor results in a functional disease quantification score of 21. In some embodiments, the functional disease quantification score may be continuously displayed while physiologic measurements are obtained. The functional disease quantification score may be continuously or periodically updated as new physiologic measurements are collected and processed to determine their effect on the traditional disease quantification score. Alternatively, the clinician could press a button on the display or on another input mechanism to request that the functional disease quantification score be updated. While the disease quantification score of 35, shown in the disease quantification score window 870 may indicate that a CABG surgery is the appropriate course of treatment, the functional disease quantification score, which incorporates additional physiology data, may indicate that PCI is a more appropriate intervention for the patient. Accordingly, in some situations where the disease quantification score is above a threshold value, the functional disease quantification score may be below that value, and thereby recommend a different intervention.

As shown in FIG. 8A, an intervention recommendation window 874 is included. The intervention recommendation window 874 may provide a visual recommendation of either CABG or PCI depending on the data. One or more images of a vessel, the visualizations in those images, and/or the measured physiological values can be used to evaluate whether to perform a first surgical procedure or a second surgical procedure. For example, the first surgical procedure can be a CABG and the second surgical procedure can be PCI.

The one or more visualizations of FIG. 8A can include or be supplemented with information regarding characteristics of the lesion or stenosis and/or the vessel using one or more other vessel data-gathering modalities. The other representations of the lesion or stenosis and/or the vessel can include, e.g., IVUS (including virtual histology), OCT, ICE, Thermal, Infrared, flow, Doppler flow, and/or other vessel data-gathering modalities. The additional information can provide a more complete and/or accurate understanding of the vessel characteristics and/or assist in evaluating a risk associated with a lesion or stenosis. For example, in some instances the information can include the occlusive value of the vessel. The occlusive value of the vessel and/or other additional information may be utilized to calculate an objective measure of the risk associated with the stenosis or lesion.

It is understood that numerous other visualization techniques may be utilized to convey the information of FIG. 8A in the context of an angiographic image or other image of the vessel (including both intravascular and extravascular imaging techniques, such as IVUS, OCT, ICE, CTA, etc.) to help the user evaluate the vessel. In that regard, while the examples of the present disclosure are provided with respect to angiographic images, it is understood that the concepts are equally applicable to other types of vessel imaging techniques, including intravascular and extravascular imaging In some instances, a user is able to select what information should be included or excluded from the displayed image. In that regard, it should be noted that these visualization techniques related to conveying the pressure measurement data in the context of an angiographic or other image of the vessel can be utilized individually and in any combinations. For example, in some implementations a user is able to select what visualization mode(s) and/or portions thereof will be utilized and the system outputs the display accordingly. Further, in some implementations the user is able to manually annotate the displayed image to include notes and/or input one or more of the measured parameters.

The images of vessels in FIG. 8A can include three-dimensional, two-dimensional, angiographic, a computed tomography angiographic (CTA), and/or other suitable forms of images. In some embodiments, a three-dimensional image may be rotated about a vertical axis. In some embodiments, a two-dimensional image may include multiple views about a vertical axis such that different two-dimensional views are shown when the image is rotated. In some implementations, the three dimensional model is displayed adjacent to a corresponding two dimensional depiction of the vessel. In that regard, the user may select both the type of depiction(s) (two dimensional (including imaging modality type) and/or three dimensional) along with what visualization mode(s) and/or portions thereof will be utilized. The system will output a corresponding display based on the user's preferences/selections and/or system defaults.

Figure 8B:
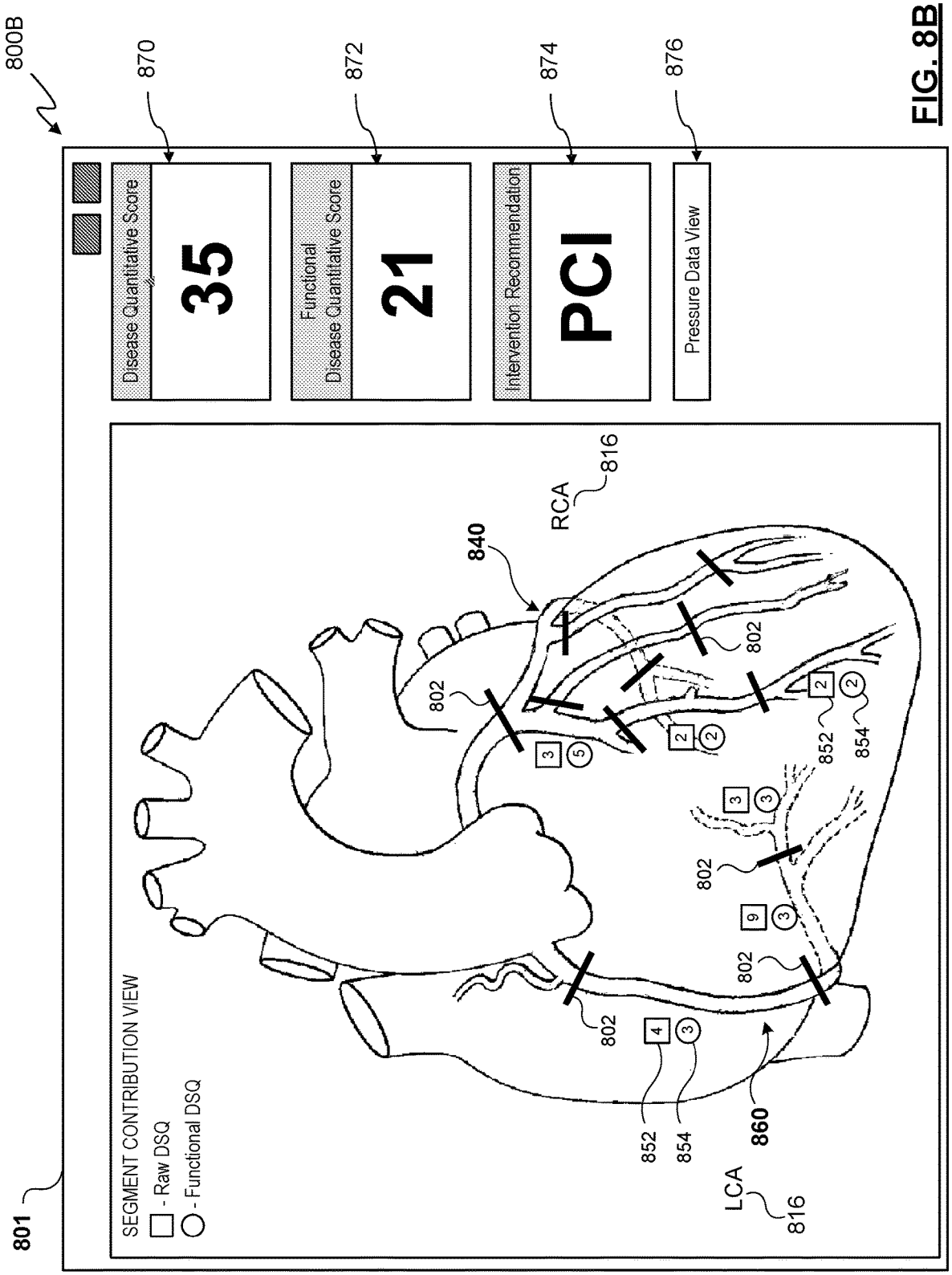
FIG. 8B is a stylized image of a patient's vasculature as seen in another user interface according to an embodiment of the present disclosure.

FIG. 8B is a diagram of a user interface 800B that includes visualizations for providing diagnostic information collected by one or more instruments at a corresponding location of the vessel on the display. The user interface 800B includes many of the features described herein in connection with the user interface 800A of FIG. 8A. The window 801 of the user interface 800B presents an angiographic image with overlaid data. While the user interface 800A includes pressure data, the user interface 800B displays markers 802 that divide the vasculature into segments according to the risk calculator used to derive the disease quantification score. In proximity to teach of the segments between the markers 802, is a disease quantification score (DSQ) indicator 852 that visually depicts the disease quantification score contribution of the associated segment. A function DSQ indicator 854 may also be presented in proximity to the segment to communicate the functional disease quantification score contributed associated with the segment. The segmentation may be performed according to the particular disease quantification score approach being implemented. For example, the segments may correspond to the segmenting used in the SYNTAX score, as described herein. In other embodiments, the representations of the contributions may be provided in colors, as used in the user interface 800A. A pressure data view button 876 may be provided in the user interface 800B to revert to the user interface 800A. A corresponding button may be present in some embodiments of the user interface 800A to switch the DSQ view of user interface 800B.

Figure 9:
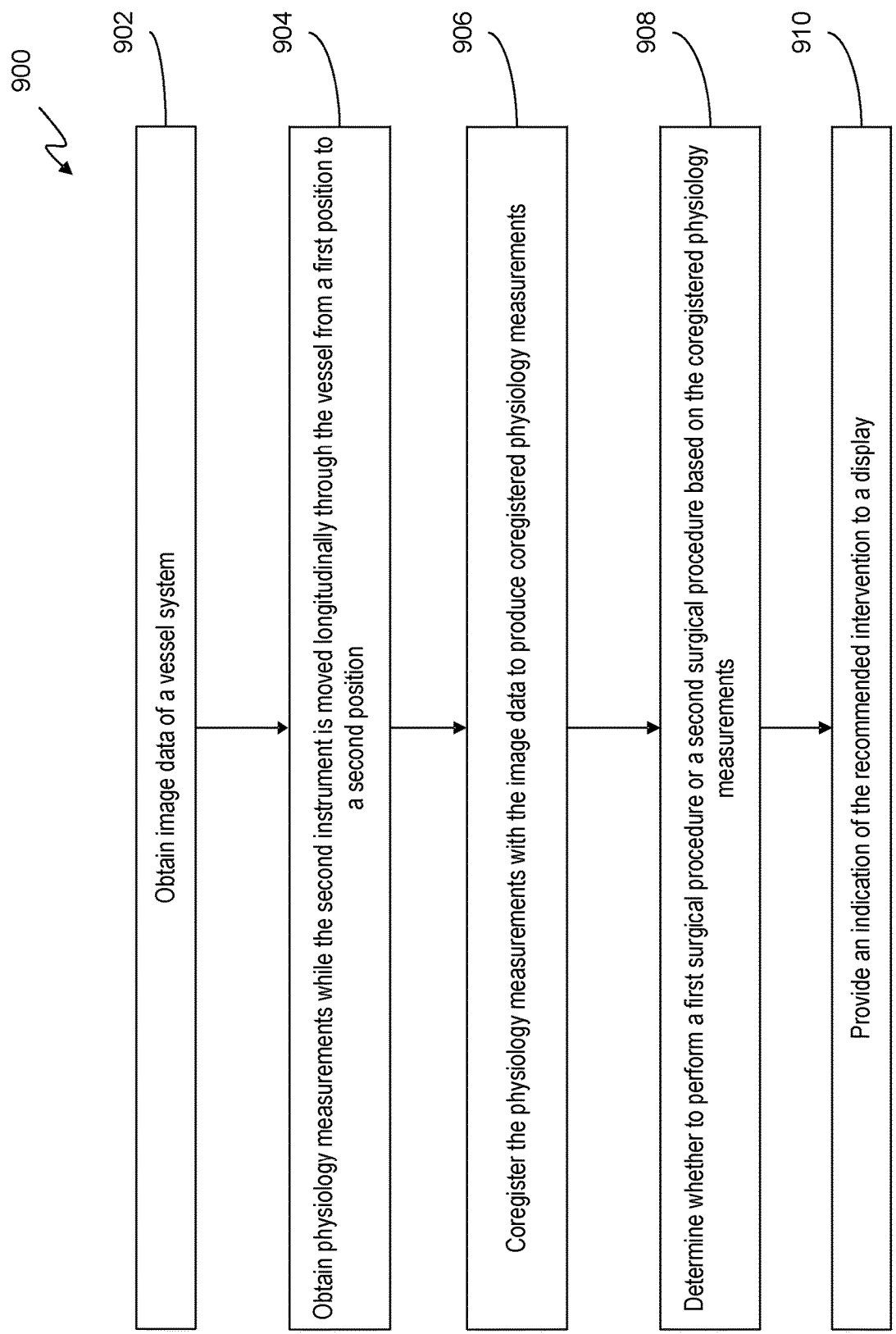
FIG. 9 is a flow diagram of a method for recommending an intervention for a patient according to an embodiment of the present disclosure.

FIG. 9 is a flow diagram of a method 900 for recommending an intervention according to an embodiment of the present disclosure. Method 900 can be implemented by a system described herein, such as system 150 of FIG. 4. As illustrated in FIG. 9, the method 900 is illustrated as a plurality of enumerated steps or operations. Embodiments of the method 900 may include additional steps or operations before, after, in between, or as part of the enumerated steps. At step 902, the method 900 includes obtaining image data from an image of a vessel system. This may be done by contacting networked storage such as an electronic health record storage system to obtain data such as angiogram data. The angiogram data may include a two dimensional angiographic image, a three dimensional angiographic image, and/or a computed tomography (CT) angiographic image. An example of the angiogram data may be seen in the user interface 500 of FIG. 5, which includes the angiogram 504. At step 904, the method 900 may include obtaining physiologic measurements from a first instrument and a second instrument positioned within the vessel of the patient while the second instrument is moved longitudinally through the vessel from a first position to a second position. One or more diagnostic measurements (e.g., pressure-based including FFR and iFR, flow-based including CFR, etc.) can be used to gather the physiologic measurements to characterize the existence and/or severity of a lesion or lesions within the vasculature of a patient. For example, when FFR is used, areas of a patient's vasculature that have a relatively high FFR (e.g., greater than 0.80) are characterized as not having a lesion or stenosis, while areas with a relatively low FFR (e.g., less than 0.80) are characterized as having a lesion or stenosis. The severity can be evaluated based on the heat map described herein. The physiologic measurements may be obtained in a manner that provides at least some location information associated with the measurements.

At step 906, the method 900 includes co-registering the physiologic measurements with the image data to produce co-registered physiologic measurements. The co-registered physiologic measurements can be displayed in an overlaid fashion, such that the physiologic measurements may be visualized in association with the angiogram image data. An example may be seen in the user interface 800A of FIG. 8A. By co-registering the physiologic measurements with the image data, the system 150 may provide additional perspective to a clinician or clinicians. The window 1102 may indicate the physical dimensions of the patient's vasculature, which may be sufficient to identify one or more lesions therein, while the physiologic measurements indicate the impact or effect of lesions with the vasculature. In some embodiments, co-registering the physiologic measurements with the image data may include associating, in a data file, each physiology measurement with a location within the vessel system, identifying a corresponding location for each physiology measurement with the image data, and associating in the co-registered physiologic measurements data file, each physiology measurement with its corresponding location within the image of the vessel system. In some embodiments, co-registering the physiologic measurements may produce a new data file that includes the co-registered physiologic measurements.

At step 908, the method 900 includes determining whether to perform a first surgical procedure over a second surgical procedure, wherein the determining is based on the co-registered physiologic measurements. The determination may result in a recommendation of the intervention for the patient. For example, the intervention recommendation may be to perform either a CABG operation or a PCI operation.

As part of the method 900, an indication of the intervention recommendation may be displayed to a clinician in a display, at step 910. As illustrated, the indication is a text-based indication. In other embodiments, another form of indication may be included.

The determining whether to perform the first surgical procedure or the second surgical procedure may include steps or operations of interpreting the image data of the vessel system, identifying one or more lesions within the vessel system, and extracting physiology information. The physiology information may include dimensions and locations of vessels, and may further include a dominance classification, a degree of occlusion of the lesion, a classification of the lesion, a degree of bending of a vessel of the vessel system, a length of the lesion, a degree of calcification of the lesion, etc. In determining whether to perform the first surgical procedure or the second surgical procedure, the method 900 may include calculating a disease quantification score from the extracted physiology information. This disease quantification score may be an image based score obtained by processing image data to provide inputs to a risk calculator. Additionally, the risk calculator may receive patient history information as an input.

In some embodiments of the method 900, evaluating whether to perform the first surgical procedure or the second surgical procedure further includes modifying or transforming the image-based disease quantification score based on the co-registered physiologic measurements to produce a functional disease quantification score. A functional disease quantification score may be lower than the image-based disease quantification score. For example, the co-registered physiologic measurements may indicate that a lesion identified from the image data may have less impact on the patient's vasculature than would be estimated from the image based on a clinician's experience alone. Accordingly, the use of the functional disease quantification score may prevent unnecessary CABG operations. In some embodiments, the image-based disease quantification score may be a SYNTAX score, while the functional disease quantification score includes a functional SYNTAX score. As part of the method 900, the disease quantification score, the functional disease quantification score, and/or an associated intervention recommendation may be displayed. In some embodiments, the intervention recommendation may be based on whether the functional disease quantification score is above a threshold value. For example, when the functional disease quantification score is above a threshold value of 30, the intervention recommendation may be for a CABG operation. When the functional disease quantification score is below the threshold value, intervention recommendation may be for a PCI procedure. The threshold value may be 30, 25, or another value suitable as the basis for intervention recommendation. For example, if the threshold value were 20, then the functional disease quantification score shown in the window 872 would be above the threshold value and the indication of the recommended intervention shown in the window 874 of FIG. 8A would be an indication to perform a CABG operation, rather than PCI.

As part of the evaluating whether to perform the first surgical procedure or the second surgical procedure, the regions of the patient anatomy and associated severity are provided to a risk calculator. These regions of the patient anatomy may be automatically segmented by image processing performed on the angiogram data. Similarly, image data may be processed to estimate the associated severity of any lesions in the segmented regions. In various embodiments, the risk calculator can include one or more algorithms for calculating the likelihood of mortality, the likelihood of success when treating the lesion or stenosis, etc. The risk calculator may output a quantity that is an objective measure of the risk associated with the patient's condition. The risk calculator may include a SYNTAX score or a fractional flow reserve (FFR)-guided SYNTAX score (SS) or functional SYNTAX score (FSS), as described in Chang-Wook Nam, et al., *Functional SYNTAX Score for Risk Assessment in Multivessel Coronary Artery Disease*, Journal of the American College of Cardiology 2011; 58(12): 1211-1218, which is incorporated by reference herein in its entirety. The risk calculator may also include any modified SYNTAX score or any numerical or otherwise objective disease quantification score that incorporates physiologic measurements, including, but not limited to, flow-based (CFR, etc.) and/or pressure-based (FFR, iFR, etc.) parameters. The risk calculator may also generate an indication of perfusion benefit and an indication of graft patency. For example, the risk calculator may quantify the predicted perfusion change should CABG be selected as the revascularization strategy.

Figure 10:
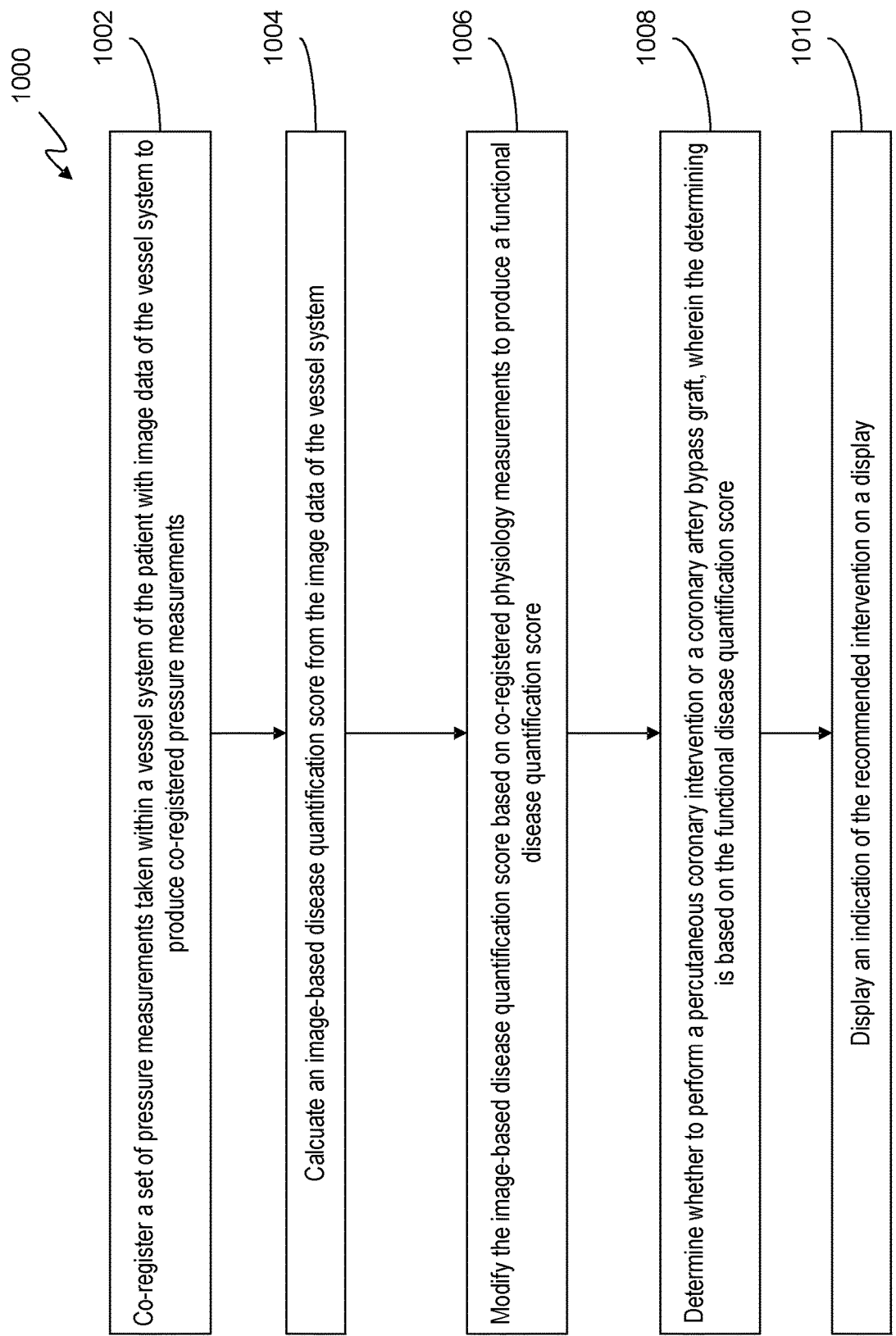
FIG. 10 is a flow diagram of another method for recommending an intervention for a patient according to an embodiment of the present disclosure.

Referring now to FIG. 10, shown therein is a flow chart of another method for generating an intervention recommendation for treating a vessel of a patient. In the illustrated embodiment, the method 1000 may begin in step 1002 in which a set of pressure measurements taken within a vessel system of the patient is co-registered with image data of the vessel system to produce co-registered pressure measurements. A processing system like the system 150 may receive data sets that include the image data and the pressure measurements and co-register them. This may be done by generating a co-registered pressure measurements data file that includes information linking a pressure measurement to a location within the vessel system or a three-dimensional model thereof.

In step 1004, the processing system calculates an image-based disease quantification score from the image data of the vessel system. This image-based disease quantification score may be a SYNTAX score as described herein. In step 1006, the processing system modifies the image-based disease quantification score based on the co-registered physiologic measurements to produce a functional disease quantification score. This functional disease quantification score may be a functional SYNTAX score, or a SYNTAX score that incorporates functional, physiologic measurements, such as pressure, flow, etc., as described herein.

In step 1006, the processing system determines whether to perform a percutaneous coronary intervention or a coronary artery bypass graft, wherein the determining is based on the functional disease quantification score. For example, when the functional disease quantification score is below a threshold, the processing system may determine that a PCI should be performed. When the functional disease quantification score is above the threshold, the processing system may determine that a CABG surgery should be performed. An indication of the recommendation intervention may be displayed on a display, in step 1008, although in some embodiments, the indication may be communicated in other ways as described herein.

Embodiments of the present disclosure may enable objective recommendations to be provided to a clinician to decide between treatment approaches. While many of the embodiments here are directed to determining whether to perform a first procedure or a second procedure, some embodiments of the disclosure may be directed to determining whether to perform a first procedure or no procedure or whether to perform a first procedure, a second procedure, or not procedure. Yet other embodiments may be directed to determining objectively whether to perform a procedure, and then determining which of two or more options to recommend based on multiple sources of data provided to a risk calculator. In some embodiments, the systems and methods may recommend both a PCI procedure and a CABG surgery. For example, a PCI procedure may be recommend for a left coronary artery, while a CABG procedure is recommended for a right coronary artery.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system, comprising:
 a pressure-sensing guidewire configured to be positioned within a vessel of a patient, wherein the pressure-sensing guidewire comprises a proximal portion, a distal portion, and a pressure sensor coupled to the distal portion; and
 a processor configured for communication with the pressure-sensing guidewire, wherein the processor is configured to:
  obtain a plurality of pressure measurements from the pressure-sensing guidewire at a plurality of locations along the vessel and a pressure-sensing instrument;
  determine, based on the plurality of pressure measurements, a plurality of pressure ratios corresponding to the plurality of locations;
  obtain an external image of the vessel;
  co-register the plurality of pressure ratios with the plurality of locations in the external image;
  determine, using a disease quantification score (DSQ) calculator, a total DSQ associated with the vessel, wherein the total DSQ [score] comprises a first contribution from a first segment of the vessel and a second contribution from a second segment of the vessel;
  generate a pressure-based view of the external image based on the plurality of pressure ratios, wherein the pressure-based view comprises a plurality of pressure ratio markers distributed along the vessel in the external image at the corresponding plurality of locations;
  generate a DSQ-based view of the external image based on the total DSQ, wherein the DSQ-based view comprises:
   the external image; and
   a first numerical value of the first contribution overlaid on the external image at a first location of the vessel specific to the first segment; and
  output, to a display in communication with the processor, a user interface comprising:
   an external image area comprising one of the pressure-based view or the DSQ-based view; and
   a numerical value of the total DSQ.

2. The system of claim 1, wherein the numerical value of the total DSQ is displayed proximate to the external image area in the user interface when the external image area comprises the pressure-based view and when the external image area comprises the DSQ-based view.

3. The system of claim 1, wherein the user interface further comprises a view button for the external image area.

4. The system of claim 1, wherein the DSQ-based view comprises further comprises a second numerical value of the second contribution overlaid on the external image at a second location of the vessel specific to the second segment.

5. The system of claim 1, wherein the pressure-based view comprises a visual representation of the plurality of pressure ratios in the external image.

6. The system of claim 5, wherein the visual representation of the plurality of pressure ratios corresponds to the plurality of pressure ratio markers.

7. The system of claim 1, wherein the total DSQ comprises an image-based DSQ.

8. The system of claim 7,
wherein the processor is configured to calculate a total functional DSQ associated with the vessel, and
wherein the user interface further comprises a visual representation of the total functional DSQ.

9. The system of claim 8,
wherein the image-based DSQ comprises a SYNTAX score, and
wherein the total functional DSQ comprises a functional SYNTAX score.

10. The system of claim 8,
wherein the total functional DSQ comprises a third contribution from the first segment of the vessel,
wherein the DSQ-based view further comprises a third numerical value of the third contribution overlaid on the external image at the first location of the vessel specific to the first segment.

11. The system of claim 3, wherein the view button is displayed proximate to the external image area in the user interface.

12. The system of claim 3, wherein the processor is further configured to receive a user input on the view button to switch the external image area to the other of the pressure-based view or the DSQ-based view.

13. The system of claim 3, wherein the view button is displayed in the user interface when the external image area comprises the pressure-based view and when the external image area comprises the DSQ-based view.

14. The system of claim 1, wherein the plurality of locations along the vessel are representative of movement of the pressure-sensing guidewire through the vessel.

15. The system of claim 14, wherein the first segment is predefined by the DSQ calculator such that the first location is distinct from the plurality of locations.

16. The system of claim 10, wherein the first numerical value comprises a first visual appearance and the third numerical value comprises a second visual appearance distinguishable from the first visual appearance.

17. The system of claim 16, wherein the first visual appearance comprises a first shape and the second visual appearance comprises a different, second shape.

* * * * *